(12) United States Patent
Omura et al.

(10) Patent No.: US 7,144,866 B2
(45) Date of Patent: *Dec. 5, 2006

(54) AVERMECTIN DERIVATIVES

(75) Inventors: Satoshi Omura, Tokyo (JP); Kenichiro Nagai, Tokyo (JP); Toshiaki Sunazuka, Chiba (JP)

(73) Assignee: The Kitasato Institute, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/343,980

(22) PCT Filed: Aug. 8, 2001

(86) PCT No.: PCT/JP01/06802

§ 371 (c)(1),
(2), (4) Date: Jul. 21, 2003

(87) PCT Pub. No.: WO02/12261

PCT Pub. Date: Feb. 14, 2002

(65) Prior Publication Data

US 2004/0018993 A1    Jan. 29, 2004

(30) Foreign Application Priority Data

Aug. 9, 2000    (JP)    ............................. 2000-240987

(51) Int. Cl.
*A61K 31/7048* (2006.01)
*C07H 17/08* (2006.01)
(52) U.S. Cl. ............................. 514/30; 514/18; 514/19; 514/29; 514/450; 514/47; 536/7.1; 544/243; 562/470
(58) Field of Classification Search .................. 514/30, 514/18, 19, 29, 450, 47; 536/7.1; 544/243; 562/470
See application file for complete search history.

(56) References Cited

U.S. PATENT DOCUMENTS

| 4,200,581 | A | 4/1980 | Fisher et al. |
| 4,427,663 | A | 1/1984 | Mrozik |
| 4,833,168 | A | 5/1989 | Wyvratt |
| 4,895,837 | A | 1/1990 | Mrozik et al. |
| 4,906,619 | A | 3/1990 | Eskola et al. |
| 5,030,622 | A | 7/1991 | Mrozik et al. |
| 5,169,839 | A | 12/1992 | Linn et al. |
| 5,206,155 | A | 4/1993 | Omura et al. |
| 5,208,222 | A | 5/1993 | Meinke et al. |
| 5,229,415 | A | 7/1993 | Linn et al. |
| 5,369,021 | A | 11/1994 | Satoshi et al. |

(Continued)

FOREIGN PATENT DOCUMENTS

| EP | 0008184 | 2/1980 |
| EP | 0351923 | 1/1990 |
| EP | 0456509 | 11/1991 |

(Continued)

OTHER PUBLICATIONS

English Language Abstract of JP 3-74397, 1991.

(Continued)

*Primary Examiner*—Shaojia Anna Jiang
*Assistant Examiner*—Devesh Khare
(74) *Attorney, Agent, or Firm*—Connolly Bove Lodge & Hutz LLP

(57) ABSTRACT

Provided is a compound represented by the general formula (I) or a salt thereof:

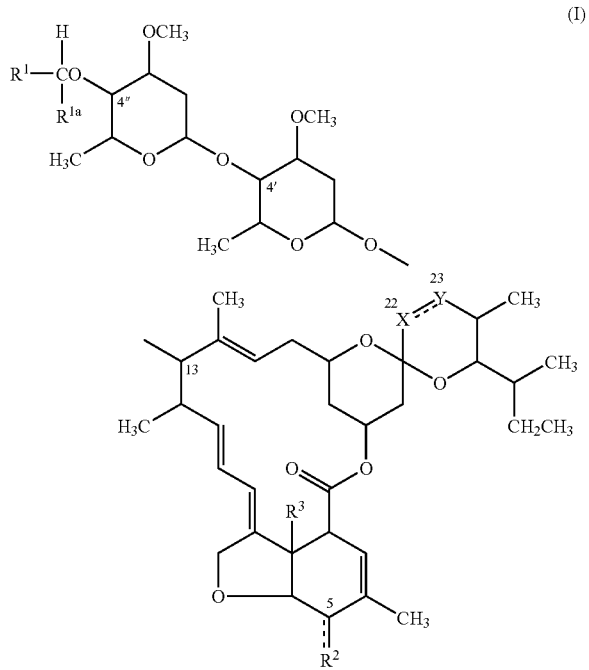

wherein, —X-----Y— represents —CH=CH— and the like, -----between $R^2$ and the carbon atom at 5-position represents a single bond or a double bond, $R^1$ represents a lower alkyl group, a formyl group, a carboxyl group, a lower alkoxycarbonyl group (wherein a lower alkyl moiety of said lower alkoxycarbonyl group may be substituted with a heterocyclic group) and the like, and $R^{1a}$ represents a hydrogen atom, provided when $R^1$ represents a lower alkoxycarbonyl group and the like, $R^{1a}$ may further represents a lower alkoxycarbonyl group and the like, when -----between $R^2$ and the carbon atom at 5-position is a single bond, $R^2$ represents a hydroxyl group and the like, and when -----between $R^2$ and the carbon atom at the 5-position is a double bound, $R^2$ combines with the carbon atom at 5-position to form a hydroxime group (—C(=NOH)) and the like, and $R^3$ represents a hydroxyl group or a tri(lower alkyl)silyloxy group.

8 Claims, No Drawings

U.S. PATENT DOCUMENTS

| | | | |
|---|---|---|---|
| 5,723,488 A | | 3/1998 | Walshe |
| 5,733,887 A | * | 3/1998 | Walshe .................. 514/28 |
| 5,883,080 A | | 3/1999 | Dutton et al. |
| 6,605,595 B1 | * | 8/2003 | Omura et al. ............... 514/30 |

FOREIGN PATENT DOCUMENTS

| | | |
|---|---|---|
| EP | 0480693 | 4/1992 |
| EP | 0506331 | 9/1992 |
| JP | 3-74397 | 3/1991 |
| JP | 3-254678 | 11/1991 |
| JP | 6-33273 | 5/1994 |
| WO | 93/18778 | 9/1993 |
| WO | 94/29328 | 12/1994 |
| WO | 95/04746 | 2/1995 |
| WO | 95/22552 | 8/1995 |

OTHER PUBLICATIONS

English Language Abstract of JP 3-254678, 1991.

Mrozik, H., et al., J. Med. Chem. 1982, 25, pp. 658-663.

Chabala, J. C., et al., J. Med. Chem. 1980, 23, pp. 1134-1136.

U.S. Appl. No. 10/343,972, filed Feb. 6, 2003 (National Stage of PCT/JP01/06803 filed Aug. 8, 2001).

Shin, et al., "Cleavage of the Spiroketal Portion of Avermectin $B_{2a}$,"Tetrahedron Letters, 1990, pp. 3525-3528, vol. 31, No. 25, Pergamon Press.

\* cited by examiner

US 7,144,866 B2

AVERMECTIN DERIVATIVES

TECHNICAL FIELD

The present invention relates to avermectin derivatives having antiparasitic activity.

BACKGROUND ART

Avermectins are antiparasitic antibiotics produced by *Streptomyces avermitilis*. Four main ingredients (A1a, A2a, B1a and B2a) have been known, and among them, avermectin B1a is known to have potent activity (Japanese Patent Unexamined Publication (KOKAI) No. (Hei) 3-254678/1991).

Various derivatives have been synthesized so far to provide avermectin derivatives having higher activity. However, these derivatives fail to have fully satisfactory antiparasitic activity.

DISCLOSURE OF THE INVENTION

An object of the present invention is to provide avermectin derivatives having antiparasitic activity.

In order to find avermectin derivatives having higher antiparasitic activity, the inventors of the present invention synthesized various derivatives using avermectin B1a, ivermectin or avermectin B2a as a starting material. As a result, they succeeded in obtaining derivatives represented by the following general formula (I) which have high antiparasitic activity. The present invention was achieved on the basis of the findings.

The present invention thus provides compounds represented by the general formula (I) or salts thereof:

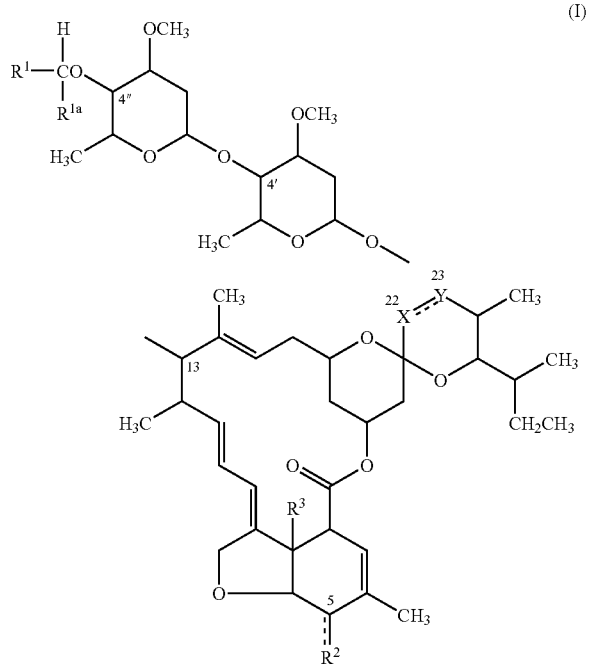

wherein, —X-----Y— represents —CH═CH—, —CH$_2$—C(═O)—, —CH$_2$—CH$_2$—, —CH$_2$—CH(R$^{13}$)— (wherein R$^{13}$ represents a hydroxyl group or a lower alkylcarbonyloxy group) or —CH$_2$—C(═N—OR$^{13c}$)— (wherein R$^{13c}$ represents a hydrogen atom or a lower alkyl group), -----between R$^2$ and the carbon atom at 5-position represents a single bond or a double bond, R$^1$ represents a substituted or unsubstituted lower alkyl group, a formyl group, a carboxyl group, a lower alkoxycarbonyl group (wherein a lower alkyl moiety of said lower alkoxycarbonyl group may be substituted with a heterocyclic group), —CH═N—OR$^4$ (wherein R$^4$ represents a hydrogen atom or a lower alkyl group), a lower alkenyloxycarbonyl group, —CH═N—NH—CONH$_2$, a cyano group, —COR$^5$ (wherein R$^5$ represents an arylalkyloxy group (wherein the aryl group may contain one or more hetero atoms as ring-constituting atoms) or —NR$^6$R$^7$ (wherein R$^6$ and R$^7$ are combined together with the adjacent nitrogen atom to form a nitrogen-containing heterocyclic group), a vinyl group substituted with a lower alkenyloxycarbonyl group, —CO—S—CH$_2$—CH$_2$—NH—CO—R$^x$ (wherein R$^x$ represents a lower alkyl group), —CH═CH—COOH, or a substituted or unsubstituted aryl group, and R$^{1a}$ represents a hydrogen atom, provided that when R$^1$ represents a lower alkoxycarbonyl group (wherein a lower alkyl moiety of said lower alkoxycarbonyl group may be substituted with a heterocyclic group) or a carboxyl group, R$^{1a}$ may further represents a lower alkoxycarbonyl group (wherein a lower alkyl moiety of said lower alkoxycarbonyl group may be substituted with a heterocyclic group), a carboxyl group, a cyano group, or an aryl group, and provided that when —X-----Y— is —CH$_2$—C(═O), —CH$_2$—CH$_2$—, or —CH$_2$—CH(R$^{13d}$)— (wherein R$^{13d}$ represents a lower alkylcarbonyloxy group), a substituent at the 4"-position may be a hydroxyl group instead of OCHR$^1$R$^{1a}$, when -----between R$^2$ and the carbon atom at 5-position is a single bond, R$^2$ represents a hydroxyl group, a lower alkoxyl group, or a tri(lower alkyl)silyloxy group, and when -----between R$^2$ and the carbon atom at the 5-position is a double bound, R$^2$ is combined with the carbon atom at 5-position to form a carbonyl group or a hydroxime group (—C(═NOH)), and R$^3$ represents a hydroxyl group or a tri(lower alkyl)silyloxy group.

Among the compounds of the general formula (I) of the present invention, the compounds or salts thereof wherein R$^2$ is a hydroxyl group are preferred. Also among the compounds of the general formula (I) of the present invention, the compounds or salts thereof wherein R$^2$ is combined with the carbon atom at 5-position to form a hydroxime group (—C(═NOH)) are preferred.

Among the aforementioned compounds, the compounds or salts thereof wherein R$^3$ is a hydroxyl group are preferred.

According to another aspect of the present invention, provided are medicaments which comprise as an active ingredient the compound represented by the aforementioned general formula (I) or a physiologically acceptable salt thereof. The medicaments can be administered as antiparasitics to a mammal including a human.

According to further aspects of the present invention, provided are use of the compound represented by the aforementioned general formula (I) or the physiologically acceptable salt thereof for the manufacture of the aforementioned medicament; and a method for therapeutic treatment of parasitosis which comprises the step of administering a therapeutically effective amount of the compound represented by the aforementioned general formula (I) or a physiologically acceptable salt thereof to a mammal including a human.

Hereinafter the compounds represented by the general formula (I) may be referred to as the compounds (I).

In the definition of each group in the compounds (I), the lower alkyl group may be any of $C_1$–$C_8$ linear, branched, and cyclic alkyl groups or a combination thereof, preferably a $C_1$–$C_8$ linear or branched alkyl group. The lower alkyl group includes, for example, a methyl group, ethyl group, propyl group, isopropyl group, cyclopropyl group, butyl group, isobutyl group, sec-butyl group, tert-butyl group, cyclopropylmethyl group, cyclobutyl group, pentyl group, hexyl group, heptyl group, and octyl group. A lower alkyl moiety in functional groups having the lower alkyl moiety, e.g., a lower alkoxyl group, a lower alkylcarbonyloxy group, a lower alkoxycarbonyl group, and a tri(lower alkyl)silyloxy group, has the same meaning as that defined in the aforementioned lower alkyl group, unless otherwise specifically mentioned. The lower alkyl moieties of the tri(lower alkyl) silyloxy group may be the same or different. The alkylene moiety of the arylalkyloxy group represented by $R^5$ is preferably a group formed by eliminating one hydrogen atom from the aforementioned lower alkyl group.

Examples of a lower alkenyl moiety in the lower alkenyloxycarbonyl group include $C_2$–$C_6$ straight and branched alkenyl groups, for example, a vinyl group, allyl group, methacryl group, butenyl group, pentenyl group, hexenyl group and the like. The number of double bonds present in the alkenyl group is not particularly limited, and preferably one.

The heterocyclic group may be either an aromatic or aliphatic heterocyclic group. Examples of the aromatic heterocyclic group include, for example, a 5- or 6-membered monocyclic aromatic heterocyclic group which contains at least one heteroatom selected from the group consisting of nitrogen, oxygen, and sulfur atoms. More specifically, examples include a pyridyl group, pyrrolyl group, furyl group, thienyl group, thiazolyl group, pyrazinyl group, imidazolyl group, pyrazolyl group, triazolyl group, tetrazolyl group, and oxazolyl group. Examples of the aliphatic heterocyclic group include, for example, a 5- or 6-membered monocyclic aliphatic heterocyclic group which contains at least one heteroatom selected from the group consisting of nitrogen, oxygen, and sulfur atoms. More specifically, examples include a pyrrolidinyl group, tetrahydrofuryl group, and tetrahydropyranyl group.

The nitrogen-containing heterocyclic group formed together with the adjacent nitrogen atom includes a morpholino group, thiomorpholino group, piperidino group, 1-piperazinyl group, and 1-pyrrolidinyl group. Among them, a morpholino group, and piperidino group are preferred.

Examples of the aryl group include, for example, a phenyl group, naphthyl group, and the like. Examples of the aryl moiety of the arylalkyloxy group represented by $R^5$ include the same examples as those mentioned above. Examples of the arylalkyloxy group containing one or more hetero atoms represented by $R^5$ include those wherein the aryl moiety is a 5- or 6-membered monocyclic aromatic heterocyclic group which contains at least one heteroatom selected from the group consisting of nitrogen, oxygen, and sulfur atoms. More specifically, examples of the aryl moiety include, for example, a pyridyl group, pyrrolyl group, furyl group, thienyl group, thiazolyl group, pyrazinyl group, imidazolyl group, pyrazolyl group, triazolyl group, tetrazolyl group, and oxazolyl group. Among them, a furyl group is preferred.

The type and number of the substituent of the substituted lower alkyl group are not particularly limited. Preferably, examples include from 1 to 3 substituents such as a hydroxyl group, a halogen atom ("a halogen atom" used herein may be any of fluorine, chlorine, bromine, and iodine atoms), an amino group, a mono(lower alkyl)amino group, a (lower alkanoyl)amino group, an aryl group, a monocyclic aromatic heterocyclic group such as those exemplified above, a lower alkanoyloxy group, an azide group, a substituted or unsubstituted arylsulfonyloxy group (the substituent of the substituted arylsulfonyloxy group is a lower alkyl group having the same meaning as that defined above), a lower alkylsulfonyloxy group, hydroxyamino group, a mono(lower alkoxy)amino group, a heterocyclic group (examples thereof include those groups exemplified for the aforementioned heterocyclic group and the nitrogen-containing heterocyclic group formed together with the adjacent nitrogen atom), a heterocyclic carbonyloxy group (i.e., heterocycle-C(=O)—O— wherein the heterocyclic moiety has the same meaning as that defined in the aforementioned heterocyclic group and the heterocyclic moiety may be substituted with a halogen atom (which has the same meaning as that defined above) or a lower alkoxycarbonyl group), a heterocyclic oxy group such as tetrahydropyranyloxy group, a carboxyl group, a lower alkoxycarbonyl group, and a cyano group (in these groups, each alkyl moiety of the mono(lower alkoxy)amino group, lower alkoxycarbonyl group, lower alkylsulfonyloxy group, mono(lower alkyl)amino group, lower alkanoylamino group and lower alkanoyloxy group has the same meaning as that defined in the aforementioned lower alkyl group, and the aryl group and aryl moieties of the arylsulfonyloxy group have the same meaning as that defined in the aforementioned aryl group).

More specifically, examples of the substituted lower alkyl group include a hydroxymethyl group, bromomethyl group, iodomethyl group, azidomethyl group, aminomethyl group, p-toluenesulfonyloxymethyl group, and the like. Further, when the substituted lower alkyl group has two or more of substituents, for example, examples of the two of substituents on the lower alkyl group include two lower alkoxycarbonyl groups (these lower alkoxycarbonyl groups have the same meaning as that defined above), two carboxyl groups, carboxyl group and cyano group, carboxyl group and an aryl group (this aryl group has the same meaning as the aforementioned aryl group). When the substituted lower alkyl group has two of substituents, methyl group is preferred as the lower alkyl group.

The type and number of the substituent of the substituted aryl group are not particularly limited. Preferably, the number of the substituent is from 1 to 5, and examples include nitro group, amino group, hydroxyl group and a halogen atom.

Salts of the compounds (I) are not particularly limited, and physiologically acceptable salts are preferred. Examples of the salts include acid-addition salts, metal salts, ammonium salts, and organic amine-addition salts. Examples of the acid-addition salts include inorganic acid salts such as hydrochlorides, sulfates, nitrates, and phosphates, and organic acid salts such as acetates, maleates, fumarates, and citrates. Examples of the metal salts include alkali metal salts such as sodium salts and potassium salts, alkaline-earth metal salts such as magnesium salts and calcium salts, aluminium salts, and zinc salts. Examples of the ammonium salts include ammonium salts and tetramethylammonium salts, and examples of the organic amine-addition salts include salts with morpholine and piperidine. When a salt of the compound (I) is used as an active ingredient of the medicament of the present invention, a physiologically acceptable salt is preferably used.

Preparations of the compounds (I) will be explained below.

Avermectin B1a, which is used as a starting material for the avermectin derivatives disclosed in the present invention, is isolated from the culture of Streptomyces avermitilis, and is a known compound (Japanese Patent Unexamined Publication No. (Hei) 3-74397/1991 and 3-254678/1991, and U.S. Pat. No. 5,206,155, and the like).

In the present invention, 5-O-tri(lower alkyl)silyl-7-O-tri (lower alkyl)silylayermectin B1a, which is used as an intermediate for the synthesis of compounds (I), can be synthesized by using avermectin B1a as a starting material according to the method described in Journal of Medicinal Chemistry (J. Med. Chem.), vol. 25, 658–663 (1982) or a similar method thereto.

Specifically, the compound can be prepared by tri(lower alkyl)silylating the 5-hydroxyl group of avermectin B1a, and then tri(lower alkyl)silylating the 7-hydroxyl group of the same.

In the present invention, 5-O-tri(lower alkyl)silyl-7-O-tri (lower alkyl)silylivermectin, which is used as an intermediate for the synthesis of compounds (I), can be prepared by tri(lower alkyl)silylating the 5-hydroxyl group of ivermectin, and then tri(lower alkyl)silylating the 7-hydroxyl group of the same.

In the present invention, 5-O-tri(lower alkyl)silyl-7-O-tri (lower alkyl)silylayermectin B2a, which is used as an intermediate for the synthesis of compounds (I), can be prepared by tri(lower alkyl)silylating the 5-hydroxyl group of avermectin B2a, and then tri(lower alkyl)silylating the 7-hydroxyl group of the same.

In the following preparations, when a defined group is changed under conditions for a method to be applied, or the group is unsuitable for carrying out the method, desired compounds can be obtained by employing introduction and elimination of a protective group conventionally used in synthetic organic chemistry [see, for example, Protective Groups in Organic Synthesis, T. W. Greene, John Wiley & Sons Inc. (1981)].

In compounds (I) obtained in Preparations 1 to 8 mentioned below, -----between $R^2$ and the carbon atom at the 5-position represents a single bond, $R^2$ represents a tri(lower alkyl)silyloxy group, and $R^3$ represents a tri(lower alkyl) silyloxy group.

Preparation 1

The compound (I) wherein $R^1$ is a lower alkoxycarbonyl group can be prepared by reacting 5-O-tri(lower alkyl)silyl-7-O-tri(lower alkyl)silylayermectin B1a with an alkyl diazoacetate derivative such as ethyl diazoacetate. The compound (I) wherein $R^1$ is a carboxyl group can be prepared by treating the above compound with a base such as alcoholic potassium hydroxide.

Preparation 2

The compound (I) wherein $R^1$ is —CON($R^6$)($R^7$) (wherein $R^6$ and $R^7$ combine together with the adjacent nitrogen atom to form a nitrogen-containing heterocyclic group) can be prepared by reacting the compound (I) wherein $R^1$ is a carboxyl group obtained in Preparation 1 with a cyclic amine compound (piperazine, morpholine and the like) in the presence of a condensing agent. Examples of the condensing agent include 1-ethyl-3-(3-dimethylaminopropyl)carbodiimide (WSCI) hydrochloride, 1,3-dicyclohexylcarbodiimide and the like.

Further, the compound (I) wherein $R^1$ is —COR$^{5a}$ (wherein R$^{5a}$ represents an arylalkyloxy group wherein the aryl group may contain one or more hetero atoms as ring-constituting atoms) can be prepared by reacting the compound (I) wherein $R^1$ is a carboxyl group with an arylalkyl alcohol (the aryl group may contain one or more hetero atoms as ring-constituting atoms) in the presence of a condensing agent.

Preparation 3

The compound (I) wherein $R^1$ is a formyl group can be prepared by reducing the compound (I) wherein $R^1$ is a carboxyl group or a lower alkoxycarbonyl group obtained in Preparation 1. As the reducing agent, sodium borohydride, lithium aluminum hydride, diisobutyl aluminum hydride or the like is used. By reacting the resulting aldehyde compound with a compound represented as $H_2N$—$OR^4$ ($R^4$ has the same meaning as that defined above), the compound can be converted into an oxime compound (hydroxime compound or alkoxime compound).

The compound (I) wherein $R^1$ is a hydroxymethyl group can be prepared by treating the compound (I) wherein $R^1$ is a carboxyl group or a lower alkoxycarbonyl group obtained in Preparation 1 with a more potent reducing agent. As such a reducing agent, lithium triethylborohydride (super hydride), and the like can be used.

Preparation 4

The compound (I) wherein $R^1$ is a substituted or unsubstituted aryl group can be prepared by reacting 5-O-tri(lower alkyl)silyl-7-O-tri(lower alkyl)silylayermectin B1a with a substituted or unsubstituted aryl halide (the substituent on the aryl group has the same meaning as that of the substituent of the aforementioned substituted aryl group, and the halide has the same meaning as that of the aforementioned halogen). For example, by reacting p-nitrobenzyl bromide as the substituted aryl halide, the compound (I) wherein $R^1$ is p-nitrophenyl group can be prepared. By reducing the resulting compound, the compound wherein $R^1$ is p-aminophenyl group can be prepared. The reduction is performed as catalytic reduction in the presence of, for example, palladium carbon catalyst. Further, the compound (I) wherein $R^1$ is p-nitrophenyl group can be subjected to deprotection reaction of the 5-position and 7-position (deprotection is performed according to Preparation 9 mentioned below), and then a reduction reaction to prepare the compound (I) wherein $R^1$ is p-aminophenyl group and wherein hydroxy groups are substituted at the 5-position and 7-position.

Preparation 5

By using the compound (I) wherein $R^1$ is a hydroxymethyl group as a starting material, another compound (I) can be prepared.

By reacting the compound (I) wherein $R^1$ is a hydroxymethyl group with a substituted or unsubstituted arylsulfonyl chloride or the like in the presence of a base, the compound (I) wherein $R^1$ is a substituted or unsubstituted arylsulfonyloxymethyl group can be prepared.

By halogenating the hydroxyl group of the compound (I) wherein $R^1$ is a hydroxymethyl group, the compound (I)

wherein $R^1$ is a halogenated methyl group can be prepared. Examples of the halogenation conditions include a reaction with triphenylphosphine/carbon tetrabromide in the presence of a base, reaction with triphenylphosphine/iodine in the presence of a base and the like.

By azidating the compound (I) wherein $R^1$ is a halogenated methyl group, the compound (I) wherein $R^1$ is azidomethyl group can be prepared. Examples of the azidation conditions include a reaction with an alkali azide such as sodium azide and potassium azide in a polar solvent and the like.

By reducing the compound (I) wherein $R^1$ is an azidomethyl group, the compound (I) wherein $R^1$ is an aminomethyl group can be prepared. Examples of the reduction conditions include those used for conventional methods such as reduction with a reduction catalyst in the presence of a source of hydrogen such as hydrogen gas and hydrazine, reduction with triphenylphosphine and the like.

By lower alkanoylating the compound (I) wherein $R^1$ is aminomethyl group, the compound (I) wherein $R^1$ is a lower alkanoylaminomethyl group can be prepared. Examples of the lower alkanoylation method include a method of reacting the compound (I) wherein $R^1$ is aminomethyl group with a lower alkanoyl halide, a method of reacting the compound (I) wherein $R^1$ is aminomethyl group with an acid anhydride, and the like.

By reacting the compound (I) wherein $R^1$ is a halogenated methyl group with $HNR^6R^7$ ($R^6$ and $R^7$ have the same meanings as those defined above), if necessary, in the presence of a base, the compound (I) wherein $R^1$ is —$CH_2NR^6R^7$ ($R^6$ and $R^7$ have the same meanings as those defined above) can be prepared.

Preparation 6

By reacting 5-O-tri(lower alkyl)silyl-7-O-tri(lower alkyl)silylayermectin B1a with an alkyl diazoacetate derivative having a substituent such as diethyl diazomalonate, ethyl diazophenylacetate, and ethyl diazocyanoacetate, the compound (I) wherein $R^1$ is a lower alkoxycarbonyl group, and $R^{1a}$ is a lower alkoxycarbonyl group (the lower alkyl moiety of the lower alkoxycarbonyl group may be substituted with a heterocyclic group), a cyano group or an aryl group can be prepared.

The substituent at the 4"-position of the compound (I) obtained above wherein $R^1$ is a lower alkoxycarbonyl group, and $R^{1a}$ is a lower alkoxycarbonyl group (the lower alkyl moiety of the lower alkoxycarbonyl group may be substituted with a heterocyclic group), a cyano group or an aryl group can be converted, for example, as follows.

The compound wherein $R^1$ and $R^{1a}$ are lower alkoxycarbonyl groups, the compound wherein $R^1$ is a lower alkoxycarbonyl group, and $R^{1a}$ is a cyano group, or the compound wherein $R^1$ is a lower alkoxycarbonyl group, and $R^{1a}$ is an aryl group can be treated under a hydrolysis condition (treatment with a base such as alcoholic potassium hydroxide etc.) to prepare the compound wherein $R^1$ and $R^{1a}$ are carboxyl groups, the compound wherein $R^1$ is a carboxyl group, and $R^{1a}$ is a cyano group, and the compound wherein $R^1$ is a carboxyl group, and $R^{1a}$ is an aryl group.

By using a diazonium salt having different lower alkyl moieties in two of the ester group moieties (e.g., diazonium salt prepared from tert-butyl ethyl malonate (($H_3C$)$_3$COOC—$CH_2$—COOCH$_2$—$CH_3$)) in the preparation of the compound (I) wherein $R^1$ and $R^{1a}$ are lower alkoxycarbonyl groups, the compound (I) wherein $R^1$ and $R^{1a}$ are different lower alkoxycarbonyl groups can be prepared. By performing selective deprotection of the ester groups, the compound (I) wherein one of $R^1$ and $R^{1a}$ is a carboxyl group, and the other is a lower alkoxycarbonyl group can also be prepared.

The aforementioned hydrolysis reaction at the 4"-position can also be performed for the compound of which 5-position and/or 7-position is deprotected, which can be obtained by deprotection of the 5-position and/or 7-position (Preparation 9 mentioned below).

Preparation 7

5-O-Tri(lower alkyl)silyl-7-O-tri(lower alkyl)silylayermectin B1a wherein $R^1$ is a lower alkenyloxycarbonyl group and 5-O-tri(lower alkyl)silyl-7-O-tri(lower alkyl)silylayermectin B1a wherein $R^1$ is a cyano group can be produced according to Preparation 1.

5-O-Tri(lower alkyl)silyl-7-O-tri(lower alkyl)silylayermectin B1a wherein $R^1$ is —CH=N—NH—CONH$_2$ can be prepared from 5-O-tri(lower alkyl)silyl-7-O-tri(lower alkyl)silylayermectin B1a wherein $R^1$ is a formyl group and $H_2N$—NH—CONH$_2$ or a salt thereof (acid addition salt etc.).

5-O-Tri(lower alkyl)silyl-7-O-tri(lower alkyl)silylayermectin B1a wherein $R^1$ is a vinyl group substituted with a lower alkenyloxycarbonyl group can be prepared by reacting 5-O-tri(lower alkyl)silyl-7-O-tri(lower alkyl)silylayermectin B1a wherein $R^1$ is a formyl group with a suitable Wittig reagent (e.g., Wittig reagent prepared from allyl diethylphosphonoacetate) or the like.

5-O-Tri(lower alkyl)silyl-7-O-tri(lower alkyl)silylayermectin B1a wherein $R^1$ is —CO—S—$CH_2$—$CH_2$—NH—CO—$R^x$ ($R^x$ has the same meaning as that defined above) can be prepared by reacting 5-O-Tri(lower alkyl)silyl-7-O-tri(lower alkyl)silylayermectin B1a wherein $R^1$ is a carboxyl group with HS—$CH_2$—$CH_2$—NH—CO—$R^x$ ($R^x$ has the same meaning as that defined above).

5-O-Tri(lower alkyl)silyl-7-O-tri(lower alkyl)silylayermectin B1a wherein $R^1$ is —CH=CH—COOH can be prepared by treating 5-O-tri(lower alkyl)silyl-7-O-tri(lower alkyl)silylayermectin B1a wherein $R^1$ is a vinyl group substituted with a lower alkenyloxycarbonyl group under a suitable deprotection condition (deprotection with acid, deprotection with a hydrogen source such as sodium borohydride, hydrogen or hydrazine in the presence of a metal catalyst such as tetrakistriphenylphosphonopalladium).

Preparation 8

The compound (I) wherein —X-----Y— is —$CH_2$—C(=O)—, —$CH_2$—$CH_2$— or —$CH_2$—CH($R^{13}$)—($R^{13}$ has the same meaning as that defined above) can also be prepared by performing a reaction similar to those of Preparations 1 to 7 mentioned above using a suitable starting material.

Among the compounds (I) mentioned above, the compound (2) wherein —X-----Y— is —$CH_2$—C(=O)— can be prepared by performing a reaction similar to those of Preparations 1 to 7 mentioned above using, as a starting material, a compound obtained by tri(lower alkyl)silylating the 5-hydroxyl group of avermectin B2a wherein a moiety corresponding to —X-----Y— is —$CH_2$—CH(—OH)— (following formula) used as a starting material, performing a selective oxidation reaction for the 23-hydroxy group and then tri(lower alkyl)silylating the 7-hydroxyl group.

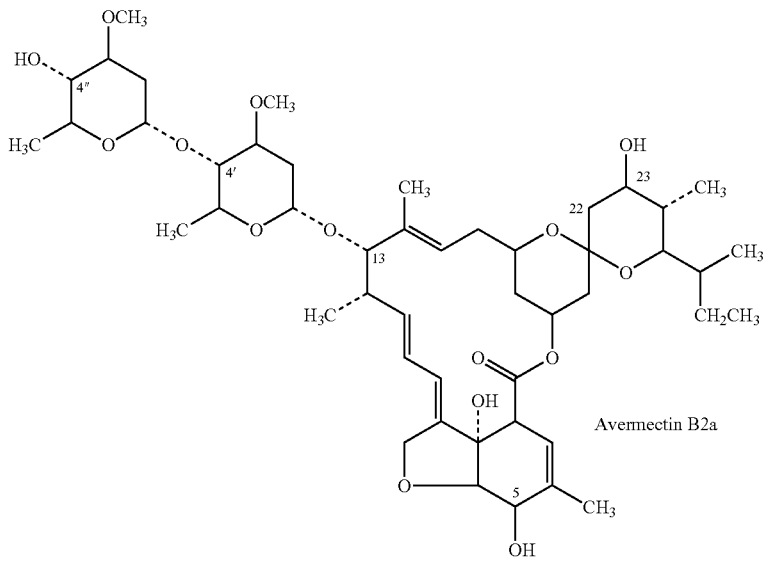

Avermectin B2a

Among the compounds (I) mentioned above, the compound (I) wherein —X- - - - -Y— is —CH$_2$—CH$_2$— can be prepared by performing a reaction similar to those of Preparation 1 to 7 mentioned above using 5-O-tri(lower alkyl)silyl-7-O-tri(loweralkyl)-silylivermection obtained in the reference examples or the like as a starting material.

Among the compounds (I) mentioned above, the compound (I) wherein —X- - - - -Y— is —CH$^2$—C(R$^{13a}$)— (wherein R$^{13a}$ represents a hydroxyl group) can be prepared by performing a reaction similar to those of Preparations 1 to 7 mentioned above using, as a starting material, a compound obtained by tri(lower alkyl)silylating the 5-hydroxyl group of avermectin B2a wherein a moiety corresponding to —X- - - - -Y— is —CH$_2$—CH(—OH)— (formula mentioned above) used as a starting material, and tri(lower alkyl)silylating the 7-hydroxyl group.

Further, among the compounds (I) mentioned above, the compound (I) wherein —X- - - - -Y— is —CH$_2$—C(R$^{13b}$)— (wherein R$^{13b}$ represents a lower alkylcarbonyloxy group having the same meaning as that defined above) can be prepared by performing a reaction similar to those of Preparations 1 to 7 mentioned above using, as a starting material, a compound obtained by tri(lower alkyl)silylating the 5-hydroxyl group of avermectin B2a wherein a moiety corresponding to —X- - - - -Y— is —CH$_2$—CH(—OH)— (formula mentioned above) used as a starting material, lower alkanoylating the 23-hydroxyl group and then tri(lower alkyl)silylating the 7-hydroxyl group.

The compound (I) wherein —X- - - - -Y— is —CH$_2$—C(=NOR$^{13c}$)— (wherein R$^{13c}$ represents a hydrogen atom or a lower alkyl group) can be prepared by reacting the 23-carbonyl group of the compound (I) wherein —X- - - - -Y— is —CH$_2$—C(=O)— used as a starting material with H$_2$N—OR$^{13c}$ (wherein R$^{13c}$ has the same meaning as that defined above) in the same manner as in Preparation 3. By further performing a reaction similar to those of Preparations 1 to 7 mentioned above, various compounds (I) wherein —X- - - - -Y— is —CH$_2$—C(=N—OR$^{13c}$)— (wherein R$^{13c}$ has the same meaning as that defined above) can be prepared.

Preparation 9

By performing deprotection of the 5-position and/or 7-position of the compounds (I) obtained in Preparation 1 to 8, the compounds (I) wherein R$^2$ and/or R$^3$ are/is a hydroxyl group can be obtained. For example, by treating the compounds obtained in Preparation 1 to 8 with a desilylating agent in a catalytic amount to an amount as a solvent in an inert solvent at a temperature of –78° C. to the boiling point of the solvent used for 1 minute to 24 hours, deprotected compounds can be obtained. As the inert solvent, tetrahydrofuran, diethyl ether, benzene, toluene, pyridine, isopropyl acetate, and the like can be used alone or in combination. Examples of the desilylating agent include hydrogen fluoride, hydrochloric acid, hydrogen bromide, sulfuric acid, hydrogen fluoride/pyridine complex and the like.

The tri(lower alkyl)silyloxy group of at the 5-position and/or 7-position may be converted into a hydroxyl group depending on the reaction conditions at the time of conversion of functional groups in other positions.

Preparation 10

When R$^2$ is a hydroxyl group, by oxidizing the hydroxyl group in a conventional manner, the compound (I) wherein R$^2$ and the carbon atom of the 5-position together form a carbonyl group can be prepared.

Furthermore, by reacting the resulting compound (I), wherein R$^2$ and the carbon atom of the 5-position combine together to form a carbonyl group, with hydroxylamine or a salt thereof (e.g., an acid addition salt such as hydrochloride) in a conventional manner, the compound (I) wherein R$^2$ and the carbon atom of the 5-position combine together to form a hydroxime group {—C(=NOH)} can also be prepared.

The aforementioned methods are shown as typical examples of the preparations of the compounds (I), and therefore, the preparations of the compounds (I) are not limited to those explained above. It can be easily understood by a person skilled in the art that the compounds of the present invention can be prepared by other methods and the compounds (I) can also be obtained by carrying out the above methods in an appropriate combination or with an appropriate modification or alteration, if necessary.

In addition, the compounds (I) can also be obtained by an appropriate combination of the methods for converting a functional group which are usually used in the field of synthetic organic chemistry. For example, the compound (I)

wherein R² is a methoxy group can be prepared by a conventional methylation of the hydroxyl group of the corresponding compound wherein R² is a hydroxyl group. Similarly, the compound (I) wherein R² is another lower alkoxyl group can be prepared by lower alkylation of the corresponding compound wherein R² is hydroxyl group.

For converting functional groups, desired conversions of functional groups can efficiently be made by protecting appropriate functional groups by methods for protection and deprotection conventionally used in the field of synthetic organic chemistry [for example, see Protective Groups in Organic Synthesis, T. W. Greene, John Wiley & Sons Inc. (1981)], if necessary.

Specific examples of the aforementioned preparation and other preparations are described in Examples, and accordingly, a person skilled in the art can prepare any compounds falling within the compound (I) by referring to the above general explanations and specific explanations in Examples, and by appropriately choosing starting materials, reagents and reaction conditions and by applying an appropriate alteration or modification, if necessary.

Purification of the desired compounds in the aforementioned preparations can be made by an appropriate combination of methods ordinarily used in the filed of synthetic organic chemistry, for example, filtration, extraction, washing, drying, concentration, crystallization, and various chromatography techniques and the like. Synthetic intermediates may be subjected to a next reaction without purification.

Isomers such as positional isomers, geometrical isomers, tautomers, and optical isomers may exist as the compounds (I). Any possible isomers and mixtures thereof in any proportion fall within the scope of the present invention. In the specification, when a bond of a functional group that substitutes on a carbon atom forming a double bond is represented by a waved line, the compound means an E- or Z-compound, or a mixture thereof.

For the preparation of a salt of the compound (I), when the compound (I) is obtained in the form of a salt, the resulting salt, per se, may be purified. When a product is obtained in a free form, a salt may be isolated and purified after dissolving or suspending the product in a suitable solvent, and adding an acid or a base thereto to form a salt. The compounds (I) and salts thereof may exist in the forms of adducts with water or various solvents (i.e., hydrates or solvates), and these adducts also fall into the scope of the present invention. Moreover, any forms of crystal also fall into the scope of the present invention.

Specific examples of the compounds (I) obtained according to the present invention are shown in Tables 1 to 4. However, the compounds of the present invention are not limited to these examples. In the tables, OTBDMS represents tert-butyldimethylsilyloxy ($OSi(CH_3)_2C(CH_3)_3$), and OTMS represents trimethylsilyloxy ($OSi(CH_3)_3$).

TABLE 1

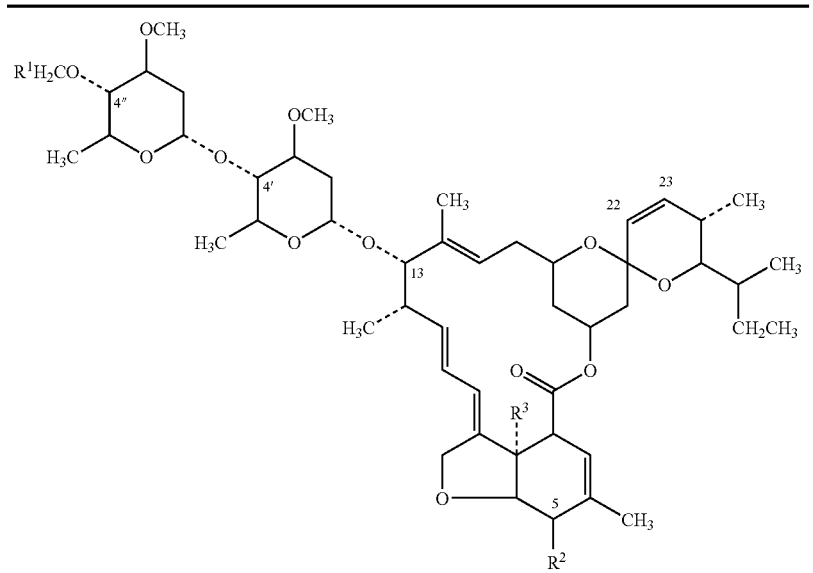

| Compound No. | R¹ | R² | R³ |
|---|---|---|---|
| 1 | CO₂CH₂CH₃ | OTBDMS | OTMS |
| 2 | CO₂CH₂CH₃ | OH | OH |
| 3 | —⟨C₆H₄⟩—NO₂ | OTBDMS | OTMS |
| 4 | —⟨C₆H₄⟩—NO₂ | OH | OH |

TABLE 1-continued

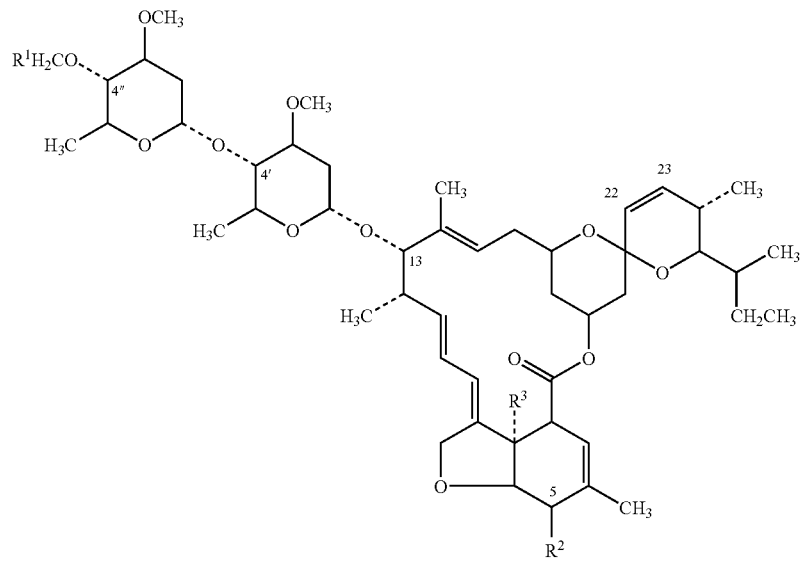

| Compound No. | R¹ | R² | R³ |
|---|---|---|---|
| 5 | ![p-aminophenyl-methyl] (4-aminobenzyl) | OH | OH |
| 6 | CO₂H | OTBDMS | OTMS |
| 7 | CO₂H | OH | OH |
| 8 | CHO | OTBDMS | OTMS |
| 9 | CH=N~OH | OH | OH |
| 10 | CO—N(morpholine) | OH | OH |
| 11 | CO—N(piperidine) | OH | OH |
| 12 | CH=N~OCH₃ | OH | OH |
| 13 | COOCH₂-(2-furyl) | OH | OH |
| 14 | CH₂OH | OTBDMS | OTMS |
| 15 | CH₂OH | OH | OH |
| 16 | CH₂OSO-C₆H₄-CH₃ | OTBDMS | OTMS |
| 17 | CH₂OSO-C₆H₄-CH₃ | OH | OH |
| 18 | CH₂Br | OTBDMS | OTMS |
| 19 | CH₂N₃ | OTBDMS | OTMS |
| 20 | CH₂N₃ | OH | OH |
| 21 | CH₂NH₂ | OTBDMS | OTMS |
| 22 | CH₂NH₂ | OH | OH |
| 23 | CH₂Br | OH | OH |
| 24 | CH₂I | OTBDMS | OTMS |
| 25 | CH₂I | OH | OH |
| 26 | CH₂NHCOCH₃ | OH | OH |

TABLE 1-continued
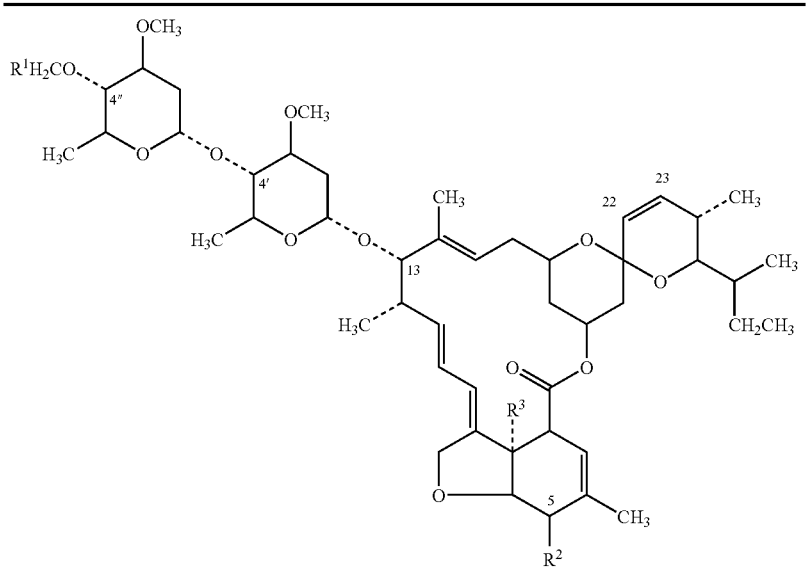
| Compound No. | $R^1$ | $R^2$ | $R^3$ |
|---|---|---|---|
| 27 | CH₂—N(piperidinyl) | OH | OH |
| 28 | CH₂—N(morpholinyl) | OH | OH |
| 29 | CH₂—N(piperazinyl)NH | OH | OH |
TABLE 2
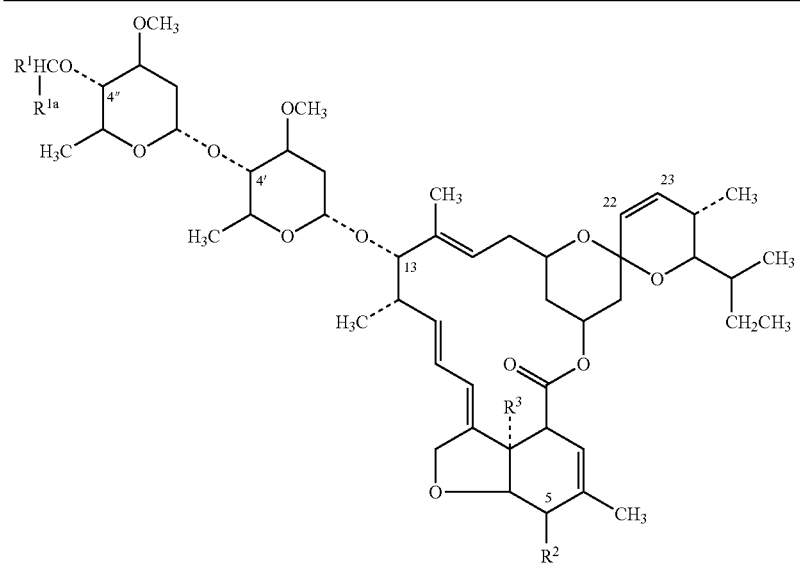
| Compound No. | $R^1$ | $R^{1a}$ | $R^2$ | $R^3$ |
|---|---|---|---|---|
| 30 | CO₂CH₂CH₃ | CO₂CH₂CH₃ | OTBDMS | OTMS |
| 31 | CO₂CH₂CH₃ | CO₂CH₂CH₃ | OH | OH |

TABLE 2-continued
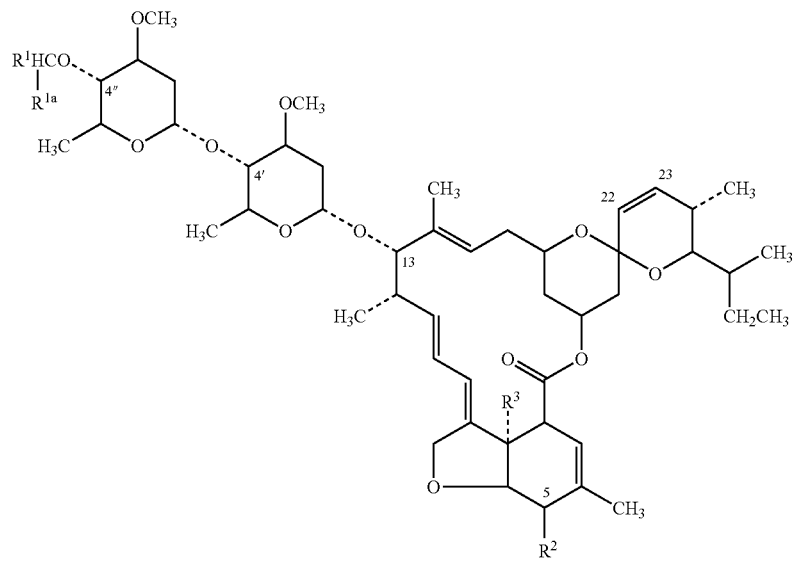
| Compound No. | R¹ | R¹ᵃ | R² | R³ |
|---|---|---|---|---|
| 32 | $CO_2H$ | CN | OH | OH |
| 33 | $CO_2H$ | $CO_2H$ | OH | OH |
| 34 | $CO_2H$ | $C_6H_5$ | OH | OH |
TABLE 3
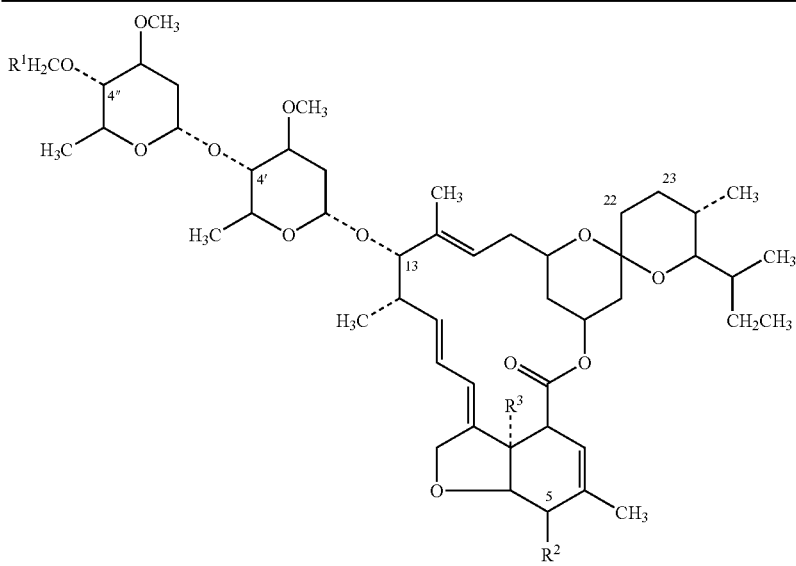
| Compound No. | R¹ | R² | R³ |
|---|---|---|---|
| 35 | $CO_2CH_2CH_3$ | OTBDMS | OTMS |
| 36 | $CO_2CH_2CH_3$ | OH | OH |
| 37 | $CH_2OH$ | OTBDMS | OTMS |
| 38 | $CH_2Br$ | OTBDMS | OTMS |
| 39 | $CO_2H$ | OH | OH |
| 40 | $CH_2OH$ | OH | OH |
| 41 | $CH_2Br$ | OH | OH |

TABLE 4

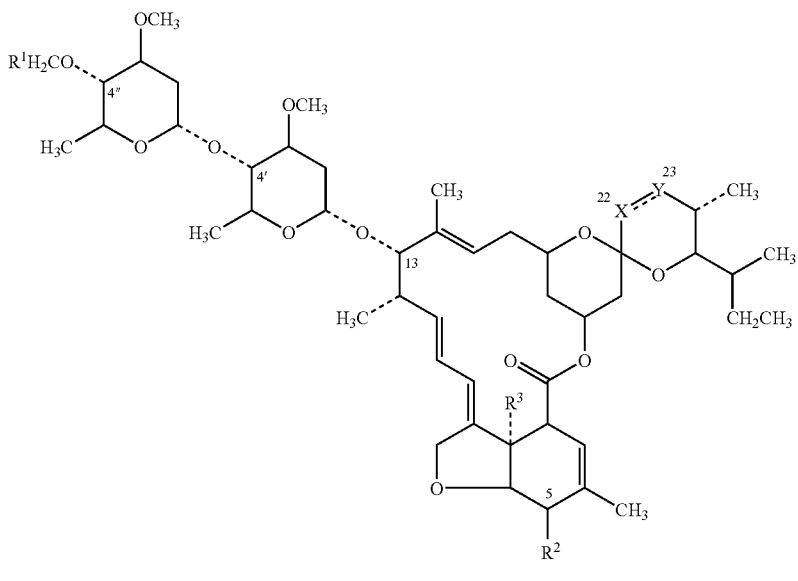

| Compound No. | $R^1$ | $R^2$ | $R^3$ | X=Y |
|---|---|---|---|---|
| 42 | $CO_2CH_2CH_3$ | OTBDMS | OTMS | $CH_2-CH(\alpha-OH)-$ |
| 43 | $CO_2CH_2CH_3$ | OH | OH | $CH_2-CH(\alpha-OH)-$ |
| 44 | $CO_2CH_2CH_3$ | OTBDMS | OTMS | $CH_2-(C=O)-$ |
| 45 | $CO_2CH_2CH_3$ | OH | OH | $CH_2-(C=O)-$ |
| 46 | $CO_2CH_2CH_3$ | OTBDMS | OTMS | $CH_2-(C=N\sim OCH_3)-$ |
| 47 | $CO_2CH_2CH_3$ | OH | OH | $CH_2-(C=N\sim OCH_3)-$ |

As the active ingredient of the medicament of the present invention, one or more substances selected from the group consisting of the compounds represented by the general formula (I) in the free form and physiologically acceptable salts thereof, and hydrates thereof and solvates thereof can be used. Any mixture of isomers or an isomer in a pure form may be used. The medicament of the present invention is generally provided in the form of a pharmaceutical composition which comprises one or more pharmaceutical additives and the aforementioned substance as an active ingredient. A route of administration is not particularly limited, and the medicament can be orally administered using preparations such as tablets, granules, capsules, syrups and powders, or parenterally administered by means of injection, intrarectal administration, transdermal administration or the like. Pharmaceutical formulations suitable for oral or parenteral administration are well-known to those skilled in the art, and they can appropriately choose pharmaceutical additives suitable for the manufacture of the pharmaceutical formulations.

The medicament of the present invention may be applied to various parasitic diseases, and the kinds of the parasitic disease are not particularly limited. The medicament of the present invention may be applied to a human or a mammal other than a human. When the medicament is applied to a mammal other than a human, the medicament may be administered as a pharmaceutical composition, or alternatively, a pharmaceutical composition or the aforementioned active ingredient, per se, may be added to a feed.

BEST MODE FOR CARRYING OUT THE INVENTION

The present invention will be explained more specifically with reference to examples. However, the present invention is not limited to these examples.

Analytical data of the compounds described in the examples were measured by using the following apparatuses. The number and structure of the compounds are the same as those described in Table 1 to 4 set out above.

IR: Horiba FT-210

NMR: JEOL (Nippon Denshi) JMN-EX270

MS: JEOL (Nippon Denshi) JMS-AX505

Solution A used in the following examples is a solution which is obtained by mixing 10 ml of hydrogen fluoride/pyridine complex, 6 ml of pyridine and 12 ml of tetrahydrofuran and stored in a polypropylene container below −10° C. 5-O-tert-Butyldimethylsilyl-7-O-trimethylsilylayermectin Ba1, used as the starting material in the following examples, was prepared by tert-butyldimethylsilylating the 5-position of avermectin B1a used as a starting material according to the method of J. Med. Chem., Vol. 25, pp. 658–663 (1982) to prepare 5-O-tert-butyldimethylsilyl-avermectin B1a, and then subjecting the product to the method of Reference Example 1.

5-O-tert-Butyldimethylsilyl-7-O-trimethylsilylivermectin, used as another starting material in the following examples, was prepared by using ivermectin as a starting material according to Reference Examples 2 and 3.

5-O-tert-Butyldimethylsilyl-7-O-trimethylsilylayermectin B2a as a further starting material used in the following examples, was prepared by using avermectin B2a as a starting material according to Reference Examples 4 and 5.

EXAMPLE 1

Preparation of Compound 1

5-O-tert-Butyldimethylsilyl-7-O-trimethylsilylayermectin B1a (2.13 g) obtained in Reference Example 1 was dissolved in dichloromethane (1 mL), and a solution of rhodium acetate (11 mg) and ethyl diazoacetate in dichloromethane (see below) was added to the solution. The solution was stirred for one day at room temperature. Diluted aqueous sodium dihydrogenphosphate solution was added to the mixture, and the mixture was extracted with dichloromethane. The organic layer was washed with water and then dried over anhydrous sodium sulfate. The solvent was evaporated under reduced pressure, and the residue was purified by column chromatography on silica gel with eluting solvents of hexane/ethyl acetate=4/1 to give 0.98 g of the desired compound (yield: 42%).

HR-FAB-MS: calcd for $C_{61}H_{100}O_{16}Si_2$ $[M+Na]^+$ 1167.6488 found 1167.6431 IR (KBr) $\lambda_{max}(cm^{-1})$:2964, 2933, 1743, 1456, 1384, 1253, 1203, 1126, 987, 838

$^1$H NMR (270 MHz, CDCl$_3$, partial data) δ (ppm): 5.78–5.48 (5H, m), 5.30 (1H, m), 5.09 (1H, m), 4.94 (1H, m), 4.80 (1H, d, J=3.0 Hz), 4.67 (1H, d, J=13.2 Hz), 4.56 (1H, d, J=15.2 Hz), 4.36 (2H, d, J=3.6 Hz), 4.25 (2H, q, J=7.5 Hz), 3.97 (1H, br.s), 3.41 (3H, s) 3.35 (3H, s), 3.27 (1H, d, J=2.3 Hz), 3.21 (1H, t, J=8.6 Hz), 2.95 (1H, t, J=8.9 Hz), 1.77 (3H, s), 1.50 (3H, s), 0.93 (9H, s), 0.14 (15H, s)

$^{13}$C NMR (67.8 MHz, CDCl$_3$) δ (ppm): 170.0, 169.2, 140.0, 136.4, 135.3, 134.8, 134.0, 127.8, 124.7, 120.4, 120.3, 118.2, 97.9, 95.4, 94.6, 84.4, 83.5, 81.3, 80.5, 78.8, 78.2, 74.3, 69.6, 68.0, 67.7 (*3), 67.1, 66.8, 60.5, 60.1, 55.9, 55.7, 46.8, 40.6, 39.4, 35.8, 34.9, 34.4, 34.0, 33.9, 30.1, 27.1, 25.5 (*3), 19.8, 19.7, 18.0, 17.6, 16.0, 14.6, 13.9, 13.8, 12.6, 11.7, 2.0 (*3), −4.8, −5.1

<Preparation of Solution of Ethyl Diazoacetate in Dichloromethane>

Glycine ethyl ester hydrochloride (2.8 g) was dissolved in two-layer solvent of water (5 mL) and dichloromethane (12 mL) and cooled to about −5° C. A cooled solution obtained by dissolving sodium nitrite (1.65 g) in water (5 mL) was added to the solution, and the mixture was stirred. Cooled 5% aqueous sulfuric acid solution (1.95 g) was further added dropwise to the mixture. The reaction mixture was stirred for about 10 minutes, while the reaction vessel was cooled so that the internal temperature did not raise over 1° C. The reaction mixture was transferred to a separating funnel to separate the aqueous layer, and then the aqueous layer was extracted with dichloromethane (15 mL). The combined organic layer was shaken with a 5% aqueous sodium hydrogencarbonate solution, and the organic layer was separated. The organic layer was dried over anhydrous calcium chloride and filtered, and the resulting solution was used for the reaction as it was.

EXAMPLE 2

Preparation of Compound 2

Compound 1 (144 mg) was dissolved in tetrahydrofuran (1.5 mL), Solution A (0.4 mL) was added to the solution, and the mixture was stirred overnight at room temperature. Pyridine was added to the reaction mixture on an ice bath, and an aqueous sodium hydrogencarbonate solution was added to the reaction mixture for neutralization, and then the mixture was extracted with ethyl acetate. The ethyl acetate layer was dried over anhydrous magnesium sulfate, and the solvent was evaporated under reduced pressure to obtain a crude product. The resulting crude product was purified by column chromatography on silica gel using stepwise elution with eluting solvents of hexane/2-propanol=15/1, 12/1, 9/1, and 6/1 to give 77 mg of the desired compound (yield: 63%).

HR-FAB-MS: calcd for $C_{52}H_{78}O_{16}$ $[M+Na]^+$ 981.5188 found 981.5234

IR (KBr) $\lambda_{max}(cm^{-1})$: 3465, 2969, 2933, 1754, 1735, 1456, 1380, 1199, 1124, 1052, 987 $^1$H NMR (270 MHz, CDCl$_3$, partial data) δ (ppm): 5.86–5.70 (4H, m), 5.54 (1H, dd, J=2.6, 9.9 Hz), 5.40 (1H, s), 5.38 (1H, m), 5.31 (1H, d, J=3.3 Hz), 4.96 (1H, m), 4.75 (1H, d, J=3.0 Hz), 4.66 (2H, s), 4.20 (2H, q, J=7.3 Hz), 4.19 (2H, d, J=4.0 Hz), 3.95 (1H, d, J=6.3 Hz), 3.91 (1H, br.s), 3.42 (3H, s), 3.35 (3H, s), 3.28 (1H, d, J=2.3 Hz), 3.19 (1H, t, J=8.9 Hz), 2.94 (1H, t, J=8.9 Hz), 1.86 (3H, s), 1.27 (3H, t, J=7.3 Hz), 1.22 (3H, d, J=6.3 Hz), 1.19 (3H, d, J=6.3 Hz), 1.15 (3H, d, J=6.9 Hz)

$^{13}$C NMR (67.8 MHz, CDCl$_3$) δ (ppm): 173.7, 170.0, 139.5, 138.0, 137.9, 136.2, 135.1, 127.7, 124.7, 120.3, 118.2, 118.0, 98.3, 95.7, 94.8, 84.8, 81.7, 80.8, 80.3, 79.2, 79.0, 78.6, 74.8, 70.0, 68.4 (*2), 68.3, 67.6 (*2), 67.1, 60.6, 56.5, 56.3, 45.6, 40.4, 39.7, 36.6, 35.1, 34.8, 34.4, 34.2, 30.5, 27.4, 20.2, 19.9, 18.3, 17.9, 16.3, 15.1, 14.2, 12.9, 12.0

EXAMPLE 3

Preparation of Compound 3

5-O-tert-Butyldimethylsilyl-7-O-trimethylsilylayermectin B1a (259 mg) was dissolved in diethyl ether (2.5 mL). p-Nitrobenzyl bromide (110 mg), diisopropylethylamine (100 μl) and silver trifluoromethanesulfonate (137 mg) were added to the solution, and the mixture was stirred at room temperature under nitrogen atmosphere for 5 hours. After an aqueous sodium hydrogencarbonate solution was added, the mixture was extracted with diethyl ether. The diethyl ether layer was dried over anhydrous magnesium sulfate, and then the solvent was evaporated under reduced pressure to give a crude product. The resulting crude product was purified by column chromatography on silica gel using stepwise elution with eluting solvents of hexane/ethyl acetate=4/1 and 3/1 to give 75 mg of the desired compound (yield: 25%). In addition, 120 mg of the starting material was recovered.

HR-FAB-MS: calcd for $C_{64}H_{99}NO_{16}Si_2$ $[M+Na]^+$ 1216.6400 found 1216.6403

IR (KBr) $\lambda_{max}$ (cm$^{-1}$): 3436, 2964, 2931, 1743, 1525, 1457, 1346, 1124, 1101, 987, 838

$^1$H NMR (270 MHz, CDCl$_3$, partial data) δ (ppm): 8.18 (2H, d, J=8.9 Hz), 7.50 (2H, d, J=8.9 Hz), 5.76–5.47 (6H, m), 5.34 (1H, d, J=3.3 Hz), 5.09 (1H, m), 4.99 (1H, d, J=12.9 Hz), 4.93 (1H, m), 4.79 (1H, d, J=3.0 Hz), 4.74 (1H, d, J=12.9 Hz), 4.66 (1H, d, J=14.5 Hz), 4.37 (1H, d, J=13.9 Hz), 4.37 (1H, d, J=5.3 Hz), 3.96 (1H, br.s), 3.41 (3H, s), 3.38 (3H, s), 3.26 (1H, s), 3.23 (1H, t, J=8.9 Hz), 3.02 (1H, t, J=8.9 Hz), 1.76 (3H, s), 1.50 (3H, s), 1.16 (3H, d, J=6.9 Hz), 0.91 (9H, s), 0.12 (15H, s)

$^{13}$C NMR (67.8 MHz, CDCl$_3$) δ (ppm): 170.4, 147.2, 146.4, 140.4, 136.6, 135.8, 135.1, 134.4, 128.0, 127.7 (*2), 125.0, 123.5 (*2), 120.7, 120.5, 118.5, 98.2, 95.7, 94.9, 84.7, 83.8, 81.7, 80.6, 79.1, 78.6, 74.7, 73.5, 69.5, 68.2, 67.9, 67.5, 67.3, 67.0, 60.3, 56.7, 56.3, 47.1, 40.8, 39.7, 36.1, 35.2, 35.1, 34.4, 34.2, 30.4, 27.4, 25.8 (*3), 20.1, 20.0, 18.4, 18.0, 16.4, 15.0, 12.9, 12.0, 2.3 (*3), −4.6, −4.8

EXAMPLE 4

Preparation of Compound 4

Compound 3 (108 mg) was dissolved in tetrahydrofuran (1.5 mL), Solution A (0.4 mL) was added to the solution, and the mixture was stirred overnight at room temperature. Pyridine was added to the mixture on ice bath, and an aqueous sodium hydrogencarbonate solution was added for neutralization, and then the mixture was extracted with ethyl acetate. The ethyl acetate layer was dried over anhydrous magnesium sulfate, and then the solvent was evaporated under reduced pressure to give a crude product. The resulting crude product was purified by column chromatography on silica gel using stepwise elution with eluting solvents of hexane/2-propanol=85/15 and 2/1 to give 80 mg of the desired compound (yield: 88%). HR-FAB-MS: calcd for $C_{55}H_{77}NO_{16}$ [M+Na]+1030.5140 found 1030.5197

IR(KBr) $\lambda_{max}(cm^{-1})$: 3463, 2967, 2931, 1716, 1606, 1523, 1454, 1380, 1346, 1160, 1120, 1103, 1052, 987

$^1$H NMR (270 MHz, CDCl$_3$, partial data) 6 (ppm): 8.19 (2H, d, J=8.9 Hz), 7.50 (2H, 8.9 Hz), 5.83–5.70 (4H, m), 5.54 (1H, dd, J=2.6, 9.9 Hz), 5.40 (1H, s), 5.38 (2H, m), 5.36 (1H, d, J=3.3 Hz), 5.00 (1H, d, J=12.8 Hz), 4.98 (1H, m), 4.75 (1H, d, J=12.8 Hz), 4.67 (2H, s), 4.27 (1H, br.s), 3.43 (3H, s), 3.40 (3H, s), 3.28 (1H, d, J=2.3 Hz), 3.21 (1H, t, J=8.9 Hz), 3.02 (1H, t, J=8.9 Hz), 1.86 (3H, s), 1.47 (3H, s)

$^{13}$C NMR (67.8 MHz, CDCl$_3$) δ (ppm): 173.7, 147.2, 146.5, 139.6, 137.9, 136.2, 135.1, 127.73 (*2), 127.66, 124.7, 123.5 (*2), 120.3, 118.2, 117.9, 98.3, 95.7, 94.8, 84.7, 81.9, 80.6, 80.3, 79.2, 79.0, 78.6, 74.8, 73.5, 68.3 (*2), 67.6, 67.3, 64.3 (*2), 56.7, 56.5, 45.6, 40.5, 39.7, 36.5, 35.1 (*2), 34.3, 34.2, 30.5, 27.4, 20.2, 19.9, 18.3, 18.0, 16.3, 15.1, 12.9, 12.0

EXAMPLE 5

Preparation of Compound 5

10% Palladium carbon (4.8 mg) was suspended in ethanol (0.2 mL) and stirred for 30 minutes under hydrogen gas atmosphere. To this suspension, Compound 4 (34 mg) dissolved in ethanol (0.6 mL) was added, and the mixture was further stirred for 2 hours. The mixture was filtered through cerite, and the residue was washed with ethanol. The ethanol solutions were combined, and the solvent was evaporated under reduced pressure to give a crude product. The resulting crude product was purified by column chromatography on silica gel using stepwise elution with eluting solvents of dichloromethane/ethyl acetate=2/1, 1.5/1, and 1/1 to give 16 mg of the desired compound (yield: 49%).

HR-FAB-MS: calcd for $C_{55}H_{79}NO_{14}$ [M+Na]$^+$ 1000.5398 found 1000.5435

IR(KBr) $\lambda_{max}(cm^{-1})$: 3448, 2966, 2931, 1724, 1456, 1380, 1340, 1288, 1160, 1120, 1054, 985

$^1$H NMR (270 MHz, CDCl$_3$, partial data) 6 (ppm): 7.15 (2H, d, J=8.4 Hz), 6.65 (2H, d, J =8.4 Hz), 5.83–5.70 (4H, m), 5.55 (1H, dd, J=2.3, 9.9 Hz), 5.42 (1H, s), 5.40 (1H, m), 5.32 (1H, m), 4.95 (1H, s), 4.75 (1H, d, J=10.2 Hz), 4.74 (1H, m), 4.68 (2H, s), 4.50 (1H, d, J=10.2 Hz), 4.29 (1H, br.s), 3.96 (1H, d, J=6.3 Hz), 3.92 (1H, br.s), 3.49 (3H, s), 3.43 (3H, s), 3.29 (1H, d, J=2.3 Hz), 3.20 (1H, t, J=8.9 Hz), 3.00 (1H, t, J=8.9 Hz), 1.87 (3H, s), 1.48 (3H, s), 1.14 (3H, d, J=6.9 Hz)

$^{13}$C NMR (67.8 MHz, CDCl$_3$) δ (ppm): 173.7, 146.1, 139.5, 138.1, 137.9, 136.3, 135.1, 129.8 (*2), 128.5, 127.7, 124.7, 120.4, 118.2, 118.0, 114.9 (*2), 98.4, 95.7, 94.8, 83.7, 81.7, 80.6, 80.3, 79.3, 79.0, 78.7, 74.9, 74.8, 68.4, 68.3, 67.71, 67.66, 67.2, 60.4, 57.4, 56.6, 45.7, 40.4, 39.7, 36.6, 35.5, 35.1, 34.4, 34.2, 30.5, 27.5, 20.1, 19.9, 18.3, 17.9, 16.3, 15.1, 12.9, 12.0

EXAMPLE 6

Preparation of Compound 6

Compound 1 was dissolved in a water/ethanol (1:1) solution (3 mL). Potassium hydroxide (45 mg) was added to the solution, and the mixture was stirred overnight at room temperature. A 3% aqueous phosphoric acid solution was added to the mixture, and the mixture was extracted with ethyl acetate. The organic layer was washed with saturated brine and then dried over anhydrous sodium sulfate. The solvent was evaporated under reduced pressure, and the residue was purified by column chromatography on silica gel using stepwise elution with eluting solvents of dichloromethane/methanol=20/1, 15/1, and 10/1 to give 118 mg of the desired compound (yield: 40%).

IR(KBr) $\lambda_{max}(cm^{-1})$: 3440, 2962, 2933, 1735, 1384, 1197, 1124, 1079, 985

$^1$H NMR (270 MHz, CDCl$_3$, partial data) 6 (ppm): 5.73 (3H, m), 5.54 (1H, dd, J=2.3, 9.9 Hz), 5.41 (1H, d, J=3.6 Hz), 5.35 (1H, m), 5.31 (1H, s), 4.97 (1H, m), 4.76 (1H, m), 4.68 (1H, d, J=16.2 Hz), 4.57 (1H, d, J=14.2 Hz), 4.42 (1H, d, J=17.2 Hz), 4.08 (1H, d, J=17.2 Hz), 3.92 (1H, br.s), 3.81 (1H, d, J=5.6 Hz), 3.49 (3H, s), 3.43 (3H, s), 3.22 (1H, t, J=9.2 Hz), 2.93 (1H, t, J=9.2 Hz), 1.78 (3H, s), 1.28 (3H, d, J=6.3 Hz), 1.23 (3H, d, J=6.3 Hz), 1.15 (3H, d, J=6.9 Hz), 0.92 (9H, s), 0.13 (6H, s)

$^{13}$C NMR (67.8 MHz, CDCl$_3$) δ (ppm): 174.1, 171.7, 140.3, 137.6, 137.4, 136.2, 135.1, 127.7, 124.9, 119.3, 118.3, 117.2, 97.9, 95.8, 94.9, 86.6, 82.0, 80.6, 80.2, 80.1, 79.3, 74.9, 70.5, 69.5, 68.4, 68.3, 67.9, 67.7, 67.0, 56.4, 55.9, 45.8, 40.4, 39.6, 36.6, 35.2, 34.4, 34.3, 30.6, 27.5, 25.9 (*3), 20.3, 20.0, 18.40, 18.37, 17.7, 16.4, 15.1, 13.0, 12.0, −4.6, −4.9 (it is considered that two peaks overlapped with other peaks)

EXAMPLE 7

Preparation of Compound 7

Compound 6 (39 mg) was dissolved in tetrahydrofuran (0.6 mL), Solution A (0.3 mL) was added to the solution, and the mixture was stirred overnight at room temperature. Pyridine was added to the mixture on an ice bath, and an aqueous sodium hydrogencarbonate solution was added for neutralization, and then the mixture was extracted with ethyl acetate. The ethyl acetate layer was dried over anhydrous magnesium sulfate, and then the solvent was evaporated under reduced pressure to give a crude product. The resulting crude product was purified by column chromatography on silica gel using stepwise elution with eluting solvents of dichloromethane/methanol=15/1, 10/1, 8/1, and 6/1 to give 11 mg of the desired compound (yield: 33%).

HR-FAB-MS: calcd for $C_{50}H_{73}O_{16}$ [M+2Na]$^+$ 975.4694 found 975.4738

IR (KBr) $\lambda_{max}(cm^{-1})$: 3459, 2967, 2933, 1733, 1454, 1382, 1122, 1052, 987

$^1$H NMR (270 MHz, CDCl$_3$, partial data) δ (ppm): 5.76 (4H, m), 5.53 (1H, dd, J=1.6, 9.9 Hz), 5.39 (3H, m), 4.97 (1H, m), 4.76 (1H, d, J=3.0 Hz), 4.66 (2H, s), 4.40 (1H, d, J=17.2 Hz), 4.28 (1H, d, J=5.6 Hz), 4.10 (1H, d, J=17.2 Hz), 3.94 (1H, d, J=6.6 Hz), 3.91 (1H, br.s), 3.47 (3H, s), 3.42

(3H, s), 3.27 (1H, br.s), 3.20 (1H, t, J=9.2 Hz), 2.92 (1H, t, J=9.2 Hz), 2.53 (1H, m), 1.85 (3H, s), 1.48 (3H, s), 1.27 (3H, d, J=6.3 Hz), 1.22 (3H, d, J=5.9 Hz), 1.15 (3H, d, J=6.6 Hz)

$^{13}$C NMR (67.8 MHz, CDCl$_3$) δ (ppm): 173.6, 172.1, 139.5, 137.8 (*2), 136.2, 135.0, 127.6, 124.7, 120.2, 118.1, 117.9, 97.9, 95.7, 94.8, 86.1, 81.8, 80.5, 80.2 (*2), 79.1, 79.0, 74.8, 70.2, 68.3 (*3), 67.5 (*2), 66.9, 56.3, 56.9, 51.3, 45.6, 40.3, 39.6, 36.5, 35.0, 34.4 (*2), 34.1, 30.4, 27.4, 20.2, 19.8, 18.3, 17.6, 16.3, 15.0, 12.9, 11.9

EXAMPLE 8

Preparation of Compound 8

Compound 1 (164 mg) was dissolved in dichloromethane (0.7 mL), a 1.0 mol/L solution of diisobutylaluminium hydride in toluene (0.5 mL) was added dropwise to the solution at −60° C., and the mixture was stirred at the same temperature for 30 minutes. After the mixture was diluted with dichloromethane, methanol was added to the mixture to inactivate excessive reagents, and cerite and sodium sulfate decahydrate were added to the mixture. The mixture was stirred for 30 minutes at room temperature. The mixture was filtered, and the residue was washed with ethyl acetate. The organic layers were combined and concentrated under reduced pressure to give a crude product. The resulting crude product was purified by column chromatography on silica gel using stepwise elution with eluting solvents of dichloromethane/methanol=60/1, 50/1, and 40/1 to give 49 mg of the desired compound (yield: 30%).

IR (KBr) λ$_{max}$(cm$^{-1}$): 3459, 2967, 2933, 1733, 1454, 1382, 1122, 1052, 987

$^1$H NMR (270 MHz, CDCl$_3$, partial data) δ (ppm): 9.66 (1H, s), 5.69 (4H, m), 5.51 (1H, dd, J=2.3, 9.9 Hz), 5.47 (1H, br.s), 5.34 (1H, m), 5.09 (1H, m), 4.93 (1H, m), 4.78 (1H, br.s), 4.65 (1H, d, J=14.8 Hz), 4.55 (1H, d, J=14.8 Hz), 4.36 (1H, br.s), 4.32 (1H, d, J=5.9 Hz), 3.39 (3H, s), 3.32 (3H, s), 3.26 (1H, d, J=2.3 Hz), 3.19 (1H, t, J=8.9 Hz), 2.90 (1H, t, J=8.9 Hz), 2.59 (1H, m), 1.75 (3H, s), 1.49 (3H, s), 1.25 (6H, m), 1.17 (3H, d, J=6.6 Hz), 0.91 (9H, s), 0.12 (15H, s)

$^{13}$C NMR (67.8 MHz, CDCl$_3$) δ (ppm) 201.2, 170.6, 140.6, 136.7, 136.0, 135.3, 134.5, 128.1, 125.2, 120.8, 120.6, 118.6, 98.2, 95.9, 95.0, 85.7, 83.9, 81.8, 80.7, 79.2, 78.5, 76.4, 74.9, 69.6, 68.4, 68.1, 67.6, 67.2, 67.1, 56.4, 56.2, 47.3, 41.0, 39.9, 36.2, 35.3, 34.8, 34.5, 34.4, 30.6, 27.5, 25.9 (*3), 20.3, 20.2, 18.5 (*2), 18.0, 16.5, 15.1, 13.0, 12.2, 2.6 (*3), −4.3, −4.5

EXAMPLE 9

Preparation of Compound 9

Compound 8 (22.7 mg) was dissolved in a mixture of pyridine (0.1 mL) and ethanol (0.1 mL), hydroxylamine hydrochloride (4.3 mg) was added to the solution, and the mixture was stirred overnight at room temperature. A saturated aqueous sodium hydrogencarbonate solution was added to the mixture, the mixture was extracted with ethyl acetate, and the organic layer was dried over anhydrous magnesium sulfate. The solvent was evaporated under reduced pressure, and the resulting crude product was dissolved in tetrahydrofuran (0.8 mL). Solution A (0.3 mL) was added to the solution, and the mixture was stirred overnight at room temperature. Pyridine was added to the mixture on an ice bath, and an aqueous sodium hydrogencarbonate solution was added for neutralization, and then the mixture was extracted with ethyl acetate. The ethyl acetate layer was dried over anhydrous magnesium sulfate, and then the solvent was evaporated under reduced pressure to give a crude product. The resulting crude product was purified on a thin layer silica gel plate with eluting solvents of hexane/2-propanol=85/15 and dichloromethane/methanol=4/1 to give 5.8 mg of the desired compound (yield: 30%).

HR-FAB-MS: calcd for C$_{50}$H$_{75}$NO$_{15}$[M+Na]+952.5034 found 952.5037

IR (KBr) X max(cm$^{-1}$): 3428, 2967, 2931, 1735, 1716, 1454, 1382, 1120, 1052, 985

EXAMPLE 10

Preparation of Compound 10

Compound 6 (121 mg) was dissolved in dichloromethane (0.5 ml), morpholine (19 μl), N-hydroxybenzotriazole (17 mg) and WSCI hydrochloride (23 mg) were added to the solution, and the mixture was stirred at room temperature for two days. A 1% aqueous phosphoric acid solution was added to the mixture, and the mixture was extracted with ethyl acetate. The organic layer was washed with water and a saturated aqueous sodium hydrogencarbonate solution and then dried over anhydrous magnesium sulfate. The solvent was evaporated under reduced pressure, and the residue was purified by column chromatography on silica gel using stepwise elution with eluting solvents of hexane/2-propanol=85/15, 4/1, and 3/1 to give a crude product.

The resulting crude product was dissolved in tetrahydrofuran (1.5 mL), Solution A (0.5 mL) was added to the solution, and the mixture was stirred overnight at room temperature. Pyridine was added to the mixture on an ice bath, and an aqueous sodium hydrogencarbonate solution was added for neutralization, and then the mixture was extracted with ethyl acetate. The ethyl acetate layer was dried over anhydrous magnesium sulfate, and then the solvent was evaporated under reduced pressure to give a crude product. The resulting crude product was purified by column chromatography on silica gel using stepwise elution with eluting solvents of dichloromethane/methanol=25/1 and 20/1 to give 74 mg of the desired compound (yield: 68%).

HR-FAB-MS: calcd for C$_{54}$H$_{81}$NO$_{16}$ [M+Na]+1022.5453 found 1022.5460

IR(KBr) λ$_{max}$(cm$^{-1}$): 3473, 2967, 2931, 1733, 1654, 1456, 1382, 1272, 1118, 1052, 987 $^1$H NMR (270 MHz, CDCl$_3$, partial data) δ (ppm): 5.77 (3H, m), 5.54 (1H, dd, J=2.3, 9.9 Hz), 5.37 (3H, m), 4.95 (1H, m), 4.75 (1H, d, J=3.0 Hz), 4.67 (1H, s), 4.51 (1H, d, J=12.8 Hz), 4.28 (1H, d, J=12.8 Hz), 4.26 (1H, s), 3.95 (1H, d, J=6.3 Hz), 3.42 (3H, s), 3.35 (3H, s), 3.28 (1H, d, J=2.0 Hz), 3.19 (1H, t, J=8.9 Hz), 2.92 (1H, t, J=8.9 Hz), 1.85 (3H, s), 1.27 (3H, d, J=6.3 Hz), 1.22 (3H, d, J=6.3 Hz), 1.15 (3H, d, J=6.9 Hz) $^{13}$C NMR (67.8 MHz, CDCl$_3$) δ (ppm): 173.7, 167.7, 139.6, 138.0, 137.9, 136.3, 135.1, 127.7, 124.7, 120.3, 118.2, 118.0, 98.2, 95.7, 94.8, 84.6, 81.8, 81.6, 80.6, 80.3, 79.2, 79.0, 78.2, 74.8, 71.8, 68.4, 68.3, 67.6, 67.2, 67.1, 66.8, 66.7, 56.5, 56.0, 45.6, 45.5, 42.0, 40.4, 39.7, 36.6, 35.1, 34.7, 34.4, 34.2, 30.5, 27.4, 20.2, 19.9, 18.3, 17.9, 16.3, 15.1, 12.9, 12.0

EXAMPLE 11

Preparation of Compound 11

Compound 6 (121 mg) was dissolved in dichloromethane (0.5 mL). Piperidine (19 μl), N-hydroxybenzotriazole (17 mg) and WSCI hydrochloride (23 mg) were added to the solution, and the mixture was stirred at room temperature for two days. A 1% aqueous phosphoric acid solution was added to the mixture, the mixture was extracted with ethyl acetate, and the organic layer was washed with water and a saturated aqueous sodium hydrogencarbonate solution and then dried over anhydrous magnesium sulfate. The solvent was evaporated under reduced pressure, and the residue was purified by column chromatography on silica gel with eluting solvents of hexane/2-propanol=85/15 to give a crude product.

The resulting crude product was dissolved in tetrahydrofuran (1.5 mL), Solution A (0.5 mL) was added to the solution, and the mixture was stirred overnight at room temperature. Pyridine was added to the mixture on an ice bath, and an aqueous sodium hydrogencarbonate solution was added for neutralization, and then the mixture was extracted with ethyl acetate. The ethyl acetate layer was dried over anhydrous magnesium sulfate, and then the solvent was evaporated under reduced pressure to give a crude product. The resulting crude product was purified by column chromatography on silica gel using stepwise elution with eluting solvents of dichloromethane/methanol=25/1 and 20/1 to give 87 mg of the desired compound (yield: 81%).

HR-FAB-MS: calcd for $C_{55}H_{83}NO_{15}$ $[M+Na]^+$ 1020.5660 found 1020.5688

IR (KBr) $\lambda_{max}(cm^{-1})$: 3471, 2967, 2933, 1737, 1718, 1645, 1452, 1382, 1160, 1120, 1052, 987

$^1$H NMR (270 MHz, $CDCl_3$, partial data) δ (ppm): 5.82–5.70 (4H, m), 5.53 (1H, dd, J=2.3, 9.9 Hz), 5.37 (3H, m), 4.91 (1H, m), 4.74 (1H, d, J=3.0 Hz), 4.66 (1H, s), 4.51 (1H, d, J=12.5 Hz), 4.26 (1H, s), 4.24 (1H, d, J=12.5 Hz), 4.03 (1H, br.s), 3.41 (3H, s), 3.36 (3H, s), 3.27 (1H, d, J=2.0 Hz), 3.19 (1H, t, J=8.9 Hz), 2.91 (1H, t, J=8.9 Hz), 1.84 (3H, s), 1.15 (3H, d, J=6.9 Hz)

$^{13}$C NMR (67.8 MHz, $CDCl_3$) δ (ppm): 173.6, 167.3, 139.5, 138.0, 137.9, 136.2, 135.1, 127.7, 124.7, 120.3, 118.2, 118.0, 98.2, 95.7, 94.8, 84.5, 81.8, 80.7, 80.3, 79.2, 79.1, 78.4, 77.2, 74.9, 71.8, 68.3 (*2), 67.6, 67.3, 67.2, 56.5, 56.2, 46.0, 45.6, 42.7, 40.4, 39.7, 36.5, 35.1, 34.8, 34.4, 34.2, 30.5, 27.4, 26.4, 25.4, 24.4, 20.1, 19.9, 18.3, 17.9, 16.3, 15.0, 12.9, 12.0

EXAMPLE 12

Preparation of Compound 12

Compound 8 (27.0 mg) was dissolved in a mixture of pyridine (0.1 mL) and ethanol (0.2 mL), methoxyamine hydrochloride (7.8 mg) was added to the solution, and the mixture was stirred at room temperature for 90 minutes. A saturated aqueous sodium hydrogencarbonate solution was added to the mixture, and the mixture was extracted with ethyl acetate. The organic layer was dried over anhydrous magnesium sulfate. The solvent was evaporated under reduced pressure, and the resulting crude product was dissolved in tetrahydrofuran (0.8 mL). Solution A (0.4 mL) was added to the solution, and the mixture was stirred overnight at room temperature. Then, the reaction mixture was treated and purified in the manners similar to those in Example 9 to give 3.9 mg of the desired compound (yield: 17%).

HR-FAB-MS: calcd for $C_{51}H_{77}NO_{15}$ $[M+Na]^+$ 966.5191 found 966.5220

IR (KBr) $\lambda_{max}(cm^{-1})$: 3457, 2966, 2933, 1733, 1456, 1380, 1160, 1120, 1047, 987

EXAMPLE 13

Preparation of Compound 13

Compound 6 (169 mg) was dissolved in dichloromethane (0.3 mL), furfuryl alcohol (50 µl), 4-dimethylaminopyridine (10 mg) and WSCI hydrochloride (63 mg) were added to the solution, and the mixture was stirred overnight at room temperature. A 5% sodium aqueous dihydrogenphosphate solution was added to the mixture, and the mixture was extracted with dichloromethane. The organic layer was washed with water and a saturated aqueous sodium hydrogencarbonate solution and then dried over anhydrous magnesium sulfate. The solvent was evaporated under reduced pressure, and the residue was purified by column chromatography on silica gel using stepwise elution with eluting solvents of hexane/ethyl acetate=4/1, 2/1, and 1/1 to give a crude product. The resulting crude product was dissolved in tetrahydrofuran (2 mL), Solution A (0.3 mL) was added to the solution, and the mixture was stirred overnight at room temperature. Pyridine was added to the mixture on an ice bath, and an aqueous sodium hydrogencarbonate solution was added for neutralization, and then the mixture was extracted with ethyl acetate. The ethyl acetate layer was dried over anhydrous magnesium sulfate, and then the solvent was evaporated under reduced pressure to give a crude product. The resulting crude product was purified by column chromatography on silica gel using stepwise elution with eluting solvents of hexane/2-propanol=12/1, 9/1, 6/1, and 3/1 to give 49 mg of the desired compound (yield: 33%).

HR-FAB-MS: calcd for $C_{55}H_{78}O_{17}$ $[M+Na]^+$ 1033.5137 found 1033.5155

IR (KBr) $\lambda_{max}(cm^{-1})$: 3467, 2967, 2933, 1735, 1452, 1382, 1294, 1165, 1191, 1122, 987

$^1$H NMR (270 MHz, $CDCl_3$, partial data) δ (ppm): 7.40 (1H, d, J=2.0 Hz), 6.44 (1H, dd, J=2.0, 3.3 Hz), 6.41 (1H, d, J=3.3 Hz), 5.85–5.69 (5H, m), 5.54 (1H, dd, J=2.3, 9.9 Hz), 5.41 (1H, s), 5.38 (1H, m), 5.32 (1H, s), 5.12 (2H, d, J=2.3 Hz), 4.96 (1H, m), 4.85 (1H, s), 4.67 (1H, s), 4.39 (2H, s), 3.42 (3H, s), 3.31 (3H, s), 3.28 (1H, d, J=2.3 Hz), 3.19 (1H, t, J=9.2 Hz), 2.94 (1H, t, J=9.2 Hz), 1.86 (3H, s), 1.27 (3H, d, J=6.3 Hz), 1.22 (3H, d, J=6.3 Hz), 1.15 (3H; d; J=6.9 Hz).

$^{13}$C NMR (67.8 MHz, $CDCl_3$) δ (ppm): 173.7, 170.2, 149.1, 143.3, 139.5, 138.1, 137.9, 136.2, 135.1, 127.7, 124.7, 120.4, 118.2, 118.0, 111.0, 110.6, 98.3, 95.7, 94.8, 84.8, 81.7, 80.8, 80.3, 79.3, 79.0, 78.5, 74.9, 69.8, 68.4, 68.3 (*2), 67.7, 67.2, 67.1, 58.0, 56.6, 56.1, 45.7, 40.4, 39.7, 36.6, 35.1, 34.8, 34.4, 34.2, 30.5, 27.5, 20.2, 19.9, 18.3, 17.9, 16.3, 15.1, 12.9, 12.0

EXAMPLE 14

Preparation of Compound 14

Compound 1 (1.10 g) was dissolved in tetrahydrofuran (2.0 mL). Under nitrogen atmosphere, a 1.0 mol/L solution of super hydride (lithium triethylbrohydride) in tetrahydrofuran (5.0 mL) was slowly added dropwise to the solution, and the mixture was stirred. After 15 minutes, water was added to the mixture to inactivate excessive reagents, and then a 30% aqueous hydrogen peroxide solution (4.0 mL) was added to the mixture, and the mixture was distributed between a 2% aqueous phosphoric acid solution and diethyl ether. The collected organic layer was washed with water and an aqueous sodium hydrogencarbonate solution and then dried over anhydrous sodium sulfate, and the solvent was evaporated under reduced pressure to give a crude product. The resulting crude product was purified by column chromatography on silica gel using stepwise elution with eluting solvents of hexane/ethyl acetate=3/1 and 1.5/1 to give 698 mg of the desired compound (yield: 66%).

HR-FAB-MS: calcd for $C_{59}H_{98}O_{15}Si_2$ [M+Na]$^+$ 1125.6342 found 1125.6417 IR (KBr) $\lambda_{max}$(cm$^{-1}$): 3455, 2962, 2933, 1743, 1457, 1382, 1253, 1203, 1124, 987, 838
$^1$H NMR (270 MHz, CDCl$_3$, partial data) δ (ppm): 5.76–5.46 (6H, m), 5.33 (1H, d, J=3.3 Hz), 5.08 (1H, m), 4.93 (1H, m), 4.77 (1H, m), 4.65 (1H, d, J=14.8 Hz), 4.54 (1H, d, J=3.3 14.5 Hz), 4.35 (1H, m), 3.95 (1H, br.s), 3.41 (3H, s), 3.39 (3H, s), 3.25 (1H, s), 3.21 (1H, t, J=8.6 Hz), 2.97 (1H, t, J=8.9 Hz), 1.75 (3H, s), 1.48 (3H, s), 1.15 (3H, d, J=6.9 Hz), 0.91 (9H, s), 0.11 (15H, s)
$^{13}$C NMR (67.8 MHz, CDCl$_3$) δ (ppm): 170.4, 140.4, 136.6, 135.8, 135.1, 134.4, 128.0, 125.0, 120.7, 120.5, 118.5, 98.0, 95.7, 94.9, 85.1, 83.8, 81.7, 80.6, 80.3, 79.1, 78.0, 74.72, 74.67, 69.5, 68.2, 68.0, 67.9, 67.4, 67.0, 62.7, 56.3, 56.2, 47.1, 40.8, 39.7, 36.1, 35.2, 34.8, 34.3, 34.2, 30.4, 27.4, 25.8 (*3), 20.1, 20.0, 18.3, 17.7, 16.3, 15.0, 12.9, 12.0, 2.3 (*3), −4.6, −4.8

EXAMPLE 15

Preparation of Compound 15

Compound 14 (107 mg) was dissolved in tetrahydrofuran (0.8 mL), Solution A (0.4 mL) was added to the solution, and the mixture was stirred overnight at room temperature. Pyridine was added to the mixture on an ice bath, and an aqueous sodium hydrogencarbonate solution was added for neutralization, and then the mixture was extracted with ethyl acetate. The ethyl acetate layer was dried over anhydrous magnesium sulfate, and then the solvent was evaporated under reduced pressure to give a crude product. The resulting crude product was purified by column chromatography on silica gel using stepwise elution with eluting solvents of dichloromethane/methanol=40/1 and 20/1 to give 79 mg of the desired compound (yield: 88%).

HR-FAB-MS: calcd for $C_{50}H_{76}O_{15}$ [M+Na]$^+$ 939.5082 found 939.5066
IR (KBr) $\lambda_{max}$(cm$^{-1}$): 3455, 2967, 2933, 1735, 1456, 1382, 1160, 1122, 1052, 985
$^1$H NMR (270 MHz, CDCl$_3$, partial data) δ (ppm): 5.88–5.71 (4H, m), 5.53 (1H, dd, J=2.6, 9.9 Hz), 5.42 (1H, s), 5.40 (1H, m), 5.37 (1H, m), 4.99 (1H, m), 4.77 (1H, d, J=3.0 Hz), 4.68 (2H, s), 4.29 (1H, br.d, J=4.6 Hz), 4.03 (1H, br.s), 3.97 (1H, d, J=6.3 Hz), 3.45 (3H, s), 3.43 (3H, s), 3.30 (1H, d, J=2.0 Hz), 3.23 (1H, t, J=8.9 Hz), 3.00 (1H, t, J=8.9 Hz), 1.87 (3H, s), 1.49 (3H, s), 1.16 (3H, d, J=6.9 Hz)
$^{13}$C NMR (67.8 MHz, CDCl$_3$) δ (ppm): 173.7, 139.6, 138.0 (*2), 136.3, 135.1, 127.7, 124.7, 120.4, 118.3, 118.0, 98.2, 95.8, 94.9, 85.2, 81.9, 80.4 (*2), 79.3, 79.1, 78.0, 74.9, 74.7, 68.4, 68.3, 68.1, 67.7, 67.2, 62.8, 60.4, 56.5, 56.4, 45.7, 40.5, 39.8, 36.6, 35.2, 34.8, 34.4, 34.2, 30.6, 27.5, 20.2, 19.9, 18.4, 17.8, 16.4, 15.1, 12.9, 12.0

EXAMPLE 16

Preparation of Compound 16

Compound 14 (0.44 g) was dissolved in pyridine (0.80 mL), tosyl chloride (0.38 g) and 4-dimethylaminopyridine (3.7 mg) were added to the solution, and the mixture was stirred at a room temperature for 2 hours. A saturated aqueous sodium hydrogencarbonate solution was added to the mixture, and the mixture was extracted with ethyl acetate. The collected ethyl acetate layer was successively washed with purified water and saturated brine and dried over anhydrous sodium sulfate. The solvent was evaporated under reduced pressure to give a crude product. The resulting crude product was purified by column chromatography on silica gel using g of Compound 16 (yield: 65%).

HR-FAB-MS: calcd for $C_{66}H_{104}O_{17}SSi_2$ [M+Na]$^+$ 1279.6431 found 1279.6379

EXAMPLE 17

Preparation of Compound 17

Compound 16 (68 mg) was dissolved in tetrahydrofuran (1.2 mL), Solution A (400 μl) was added to the solution, and the mixture was stirred overnight at room temperature. Then, the reaction mixture was treated and purified in the manners similar to those in Example 2 to give 62 mg of the desired compound (yield: 83%). HR-FAB-MS: calcd for $C_{57}H82O17S$ [M+Na]$^+$ 1093.5170 found 1093.5127

EXAMPLE 18

Preparation of Compound 18

Compound 14 (0.30 g) was dissolved in dichloromethane (2.7 mL), triethylamine (0.38 mL), triphenylphosphine (0.18 g) and carbon tetrabromide (0.22 g) were added to the solution, and the mixture was stirred at room temperature for 30 minutes. A saturated aqueous sodium hydrogencarbonate solution was added to the mixture, and then the mixture was extracted with dichloromethane. The collected dichloromethane layer was washed with saturated brine and dried over anhydrous sodium sulfate. The solvent was evaporated under reduced pressure to give a crude product. The resulting crude product was purified by column chromatography on silica gel with eluting solvents of hexane/ethyl acetate=5/1 to give 0.29 g of the desired substance (yield: 91%).

IR(KBr) $\lambda_{max}$(cm$^{-1}$): 3423, 2964, 2933, 1743, 1458, 1383, 1340, 1306, 1254, 1203, 1161, 1124, 1101, 1054, 987
$^1$H NMR (270 MHz, CDCl$_3$, partial data) δ (ppm): 5.66 (4H, m), 5.50 (1H, dd, J=2.3, 9.9 Hz), 5.47 (1H, br.d, J=2.3 Hz), 5.30 (1H, d, J=3.0 Hz), 5.10 (1H, m), 4.93 (1H, m), 4.86 (1H, d, J=3.3 Hz), 4.66 (1H, d, J=14.2 Hz), 4.55 (1H, d, J=14.1 Hz), 4.37 (1H, m), 3.96 (1H, br.s), 3.81 (1H, d, J=5.3 Hz), 3.46 (2H, t, J=6.2 Hz), 3.41 (6H, s), 3.26 (1H, d, J=2.0 Hz), 3.21 (1H, t, J=8.9 Hz), 2.86 (1H, t, J=9.1 Hz), 2.57 (1H, m), 1.76 (3H, s), 1.50 (3H, s), 1.28 (3H, d, J=6.6 Hz), 1.23 (3H, d, J=6.9 Hz), 1.16 (3H, d, J=6.9 Hz), 0.92 (9H, s), 0.13 (15H, s)
$^{13}$C NMR (67.8 MHz, CDCl$_3$) δ (ppm): 170.5, 140.4, 136.7, 135.8, 135.2, 134.4, 128.0, 125.0, 120.7, 120.5, 118.5, 98.3, 95.8, 94.9, 84.8, 83.8, 81.7, 80.7, 80.6, 79.1, 78.3, 74.7, 72.6, 69.5, 68.3, 68.0, 67.5 (*2), 67.0, 57.0, 56.4, 47.2, 40.9, 39.7, 36.1, 35.2 (*2), 34.4, 34.2, 31.0, 30.4, 27.4, 25.8 (*3), 20.2, 20.1, 18.4 (*2), 17.9, 16.4, 15.0, 12.9, 12.1, 2.4 (*3), −4.5, −4.8

EXAMPLE 19

Preparation of Compound 19

Compound 18 (0.30 g) was dissolved in dimethyl sulfoxide (2.6 mL), sodium azide (33 mg) was added to the solution, and the mixture was stirred at 40° C. for 4.5 hours. Purified water was added to the mixture, and then the mixture was extracted with ethyl acetate. The collected ethyl acetate layer was washed with water and dried over anhydrous magnesium sulfate. The solvent was evaporated under reduced pressure to give a crude product. The resulting crude product was purified by column chromatography on silica gel with eluting solvents of hexane/ethyl acetate=5/1 to give 0.28 g of the desired substance (yield: 95%).

HR-FAB-MS: calcd for $C_{59}H_{97}O_{14}N_3Si_2Na$ $[M+Na]^+$ 1150.6407 found 1150.6395

IR(KBr) $\lambda_{max}(cm^{-1})$: 3429, 2962, 2933, 2104, 1743, 1460, 1385, 1338, 1309, 1252, 1205, 1161, 1124, 1083, 1055, 987

$^1H$ NMR (270 MHz, CDCl$_3$, partial data) δ (ppm): 5.65 (4H, m), 5.49 (1H, dd, J=2.0, 9.9 Hz), 5.46 (1H, br.s), 5.30 (1H, d, J=3.0 Hz), 5.09 (1H, m), 4.92 (1H, m), 4.77 (1H, d, J=2.6 Hz), 4.64 (1H, d, J=14.7 Hz), 4.53 (1H, d, J=14.7 Hz), 4.36 (1H, m), 3.95 (1H, br.s), 3.80 (1H, d, J=5.3 Hz), 3.40 (3H, s), 3.39 (3H, s), 3.25 (1H, d, J=2.3 Hz), 3.20 (1H, t, J=8.9 Hz), 2.83 (1H, t, J=8.9 Hz), 2.55 (1H, m), 1.75 (3H, s), 1.48 (3H, s), 1.25 (3H, d, J=6.9 Hz), 1.22 (3H, d, J=6.9 Hz), 1.15 (3H, d, J=6.9 Hz), 0.91 (9H, s), 0.11 (15H, s)

$^{13}C$ NMR (67.8 MHz, CDCl$_3$) δ (ppm): 170.4, 140.3, 136.6, 135.8, 135.1, 134.3, 127.9, 124.9, 120.7, 120.5, 118.5, 98.2, 95.7, 94.9, 84.8, 83.7, 81.7, 80.6, 80.5, 79.1, 78.2, 74.7, 71.4, 69.4, 68.2, 67.9, 67.4 (*2), 67.0, 56.7, 56.3, 51.2, 47.1, 40.8, 39.7, 36.1, 35.2, 35.0, 34.3, 34.2, 30.4, 27.4, 25.8 (*3), 20.1, 20.0, 18.3 (*2), 17.7, 16.3, 15.0, 12.9, 12.0, 2.3 (*3), −4.6, −4.8

EXAMPLE 20

Preparation of Compound 20

Compound 19 (50 mg) was dissolved in tetrahydrofuran (500 μl), Solution A (50 μl) was added to the solution, and the mixture was stirred overnight at room temperature. Then, the reaction mixture was treated and purified in the manners similar in those in Example 9 to give 36 mg of the desired compound (yield: 87%).

HR-FAB-MS: calcd for $C_{50}H_{75}O_{14}N_3$ $[M+Na]^+$ 964.5147 found 964.5145

IR(KBr) $\lambda_{max}(cm^{-1})$: 3675, 2968, 2933, 2162, 1718, 1452, 1383, 1344, 1294, 1196, 1163, 1120, 1051, 987

$^1H$ NMR (270 MHz, CDCl$_3$, partial data) δ (ppm): 5.86 (1H, m), 5.74 (3H, m), 5.54 (1H, dd, J=2.6, 9.9 Hz), 5.41 (1H, br.s), 5.40 (1H, m), 5.34 (1H, d, J=3.0 Hz), 4.97 (1H, m), 4.73 (1H, d, J=3.0 Hz), 4.67 (2H, s), 4.28 (1H, m), 3.96 (1H, d, J=6.6 Hz), 3.93 (1H, br.s), 3.43 (6H, s), 3.29 (1H, d, J=2.0 Hz), 3.21 (1H, t, J=9.1 Hz), 2.85 (1H, t, J=9.1 Hz), 2.53 (1H, m), 1.87 (3H, s), 1.48 (3H, s), 1.27 (3H, d, J=6.3 Hz), 1.23 (3H, d, J=5.9 Hz), 1.16 (3H, d, J=6.9 Hz)

$^{13}C$ NMR (67.8 MHz, CDCl$_3$) δ (ppm): 173.7, 139.6, 138.0 (*2), 136.3, 135.1, 127.7, 124.9, 120.4, 118.2, 118.0, 98.3, 95.7, 94.9, 84.9, 81.8, 80.6, 80.3, 79.3, 79.0, 78.3, 74.9, 71.4, 68.4, 68.3, 67.9, 67.7, 67.5, 67.2, 56.8, 56.6, 51.3, 45.7, 40.4, 39.7, 36.6, 35.1 (*2), 34.5, 34.2, 30.5, 27.5, 20.2, 19.9, 18.3, 17.8, 16.3, 15.1, 12.9, 12.0

EXAMPLE 21

Preparation of Compound 21

Compound 19 (0.25 g) was dissolved in tetrahydrofuran (2.2 mL), triphenylphosphine (0.12 g) was added to the solution, and the mixture was stirred at 40° C. for 2.5 hours. Purified water and 30% aqueous ammonia (2 drops) were added to the mixture, and the mixture was extracted with ethyl acetate. The collected ethyl acetate layer was washed with water and dried over anhydrous sodium sulfate. The solvent was evaporated under reduced pressure to give a crude product. The resulting crude product was purified by column chromatography on silica gel with eluting solvents of chloroform/methanol=50/1 to give 0.24 g of the desired substance (yield: 100%). As chloroform for the eluting solvent, ten drops of 30% aqueous ammonia was added dropwise to 100 mL of chloroform and used.

HR-FAB-MS: calcd for $C_{59}H_{99}O_{14}NSi_2$ $[M+Na]^+$ 1124.6502 found 1124.6499

IR(KBr) $\lambda_{max}(cm^{-1})$: 3467, 2964, 2933, 1743, 1458, 1383, 1338, 1306, 1254, 1203, 1161, 1124, 1057, 987

$^1H$ NMR (270 MHz, CDCl$_3$, partial data) δ (ppm): 5.70 (4H, m), 5.51 (1H, dd, J=2.3, 9.9 Hz), 5.48 (1H, br.d, J=2.0 Hz), 5.31 (1H, d, J=3.0 Hz), 5.10 (1H, m), 4.94 (1H, m), 4.79 (1H, d, J=2.6 Hz), 4.66 (1H, d, J=14.1 Hz), 4.56 (1H, d, J=14.1 Hz), 4.37 (1H, m), 3.96 (1H, br.s), 3.82 (1H, d, J=5.3 Hz), 3.41 (6H, s), 3.24 (2H, m), 2.87 (1H, t, J=9.1 Hz), 2.57 (1H, m), 1.77 (3H, s), 1.50 (3H, s), 1.25 (3H, d, J=6.3 Hz), 1.24 (3H, d, J=5.6 Hz), 1.17 (3H, d, J=6.9 Hz), 0.92 (9H, s), 0.13 (15H, s)

$^{13}C$ NMR (67.8 MHz, CDCl$_3$) δ (ppm): 170.5, 140.4, 136.7, 135.9, 135.2, 134.4, 128.0, 125.0, 120.7, 120.5, 118.5, 98.2, 95.8, 95.0, 84.8, 83.8, 81.7, 80.7, 80.5, 79.2, 78.1, 74.8, 69.5 (*2), 68.3, 68.0, 67.8, 67.5, 67.0, 56.7, 56.4, 47.2, 42.0, 40.0, 39.8, 36.1, 35.2, 35.0, 34.4, 34.3, 30.5, 27.4, 25.8 (*3), 20.2, 20.1, 18.4 (*2), 17.9, 16.4, 15.0, 12.9, 12.1, 2.4 (*3), −4.5, −4.7

EXAMPLE 22

Preparation of Compound 22

Compound 21 (70 mg) was dissolved in tetrahydrofuran (1.0 mL), Solution A (70 μl) was added to the solution, and the mixture was stirred overnight at room temperature. Then, the mixture was treated in the manner similar to that in Example 2. The resulting product was purified by column chromatography on silica gel with eluting solvents of chloroform/methanol=20/1 to give 54 mg of the desired compound (yield: 92%). As chloroform for the eluting solvent, ten drops of 30% aqueous ammonia was added dropwise to 100 mL of chloroform and used. HR-FAB-MS: calcd for $C_{50}H_{77}O_{14}N$ $[M+Na]^+$ 938.5242 found 938.5243

IR(KBr) $\lambda_{max}(cm^{-1})$: 3481, 2966, 2931, 2162, 1722, 1456, 1383, 1342, 1294, 1194, 1163, 1120, 1055, 987 $^1H$ NMR (270 MHz, CDCl$_3$, partial data) δ (ppm): 5.84 (1H, m), 5.75 (3H, m), 5.53 (1 dd, J=2.5, 9.7 Hz), 5.40 (1H, br.s), 5.36 (1H, m), 5.32 (1H, d, J=3.0 Hz), 4.96 (1H, m), 4.75 (1H, d, J=3.3 Hz), 4.66 (2H, s), 4.27 (1H, br.d, J=5.9 Hz), 3.94 (1H, d, J=6.3 Hz), 3.91 (1H, s), 3.42 (6H, s), 3.27 (1H, d, J=2.0 Hz), 3.20 (1H, t, J=8.9 Hz), 2.85 (1H, t, J=8.9 Hz), 2.30 (1H, m), 1.85 (3H, s), 1.47 (3H, s), 1.24 (3H, d, J=5.6 Hz), 1.22 (3H, d, J=5.6 Hz), 1.14 (3H, d, J=5.6 Hz)

$^{13}C$ NMR (67.8 MHz, CDCl$_3$) δ (ppm): 173.6, 139.6, 137.9, 137.8, 136.2, 135.1, 127.7, 124.7, 120.3, 118.2, 118.0, 98.2, 95.7, 94.8, 84.7, 81.8, 80.5, 80.3, 79.3, 79.2, 78.1, 74.8, 68.3 (*3), 67.7, 67.6 (*2), 67.2, 56.8, 56.5, 45.7, 42.2, 40.4, 39.7, 36.6, 35.1 (*2), 34.4, 34.2, 30.5, 27.4, 20.1, 19.9, 18.3, 17.9, 16.3, 15.0, 12.9, 12.0

EXAMPLE 23

Preparation of Compound 23

Compound 18 (0.42 g) was dissolved in tetrahydrofuran (0.50 mL), Solution A (50 μl) was added to the solution, and the mixture was stirred overnight at room temperature.

Then, the reaction mixture was treated and purified in the manners similar to those in Example 2 to give 0.31 g of the desired compound (yield: 89%).

HR-FAB-MS: calcd for $C_{50}H_{75}O_{14}Br$ [M+Na]$^+$ 1001.4238 found 1001.4243

IR(KBr) $\lambda_{max}$(cm$^{-1}$): 3446, 2968, 2933, 1712, 1454, 1381, 1340, 1274, 1194, 1161, 1120, 1053, 985

$^1$H NMR (270 MHz, CDCl$_3$, partial data) δ (ppm): 5.83 (1H, m), 5.73 (3H, m), 5.53 (1 dd, J=2.3, 9.7 Hz), 5.40 (1H, br.s), 5.36 (1H, m), 5.31 (1H, d, J=3.3 Hz), 4.97 (1H, m), 4.75 (1H, d, J=3.3 Hz), 4.67 (2H, s), 4.22 (1H, m), 4.12 (1H, m), 4.02 (1H, br.s), 3.95 (1H, d, J=6.3 Hz), 3.91 (1H, br.s), 3.45 (2H, d, J=6.3 Hz), 3.42 (6H, s), 3.28 (1H, d, J=2.3 Hz), 3.19 (1H, t, J=8.9 Hz), 2.86 (1H, t, J=8.9 Hz), 2.51 (1H, m), 2.00 (1H, m), 1.85 (3H, s), 1.76 (1H, m), 1.47 (3H, s), 1.27 (3H, d, J=6.3 Hz), 1.22 (3H, d, J=6.3 Hz), 1.14 (3H, d, J=6.9 Hz)

$^{13}$C NMR (67.8 MHz, CDCl$_3$) δ (ppm): 173.7, 139.6, 138.0, 137.9, 136.2, 135.1, 127.7, 124.7, 120.3, 118.2, 118.0, 98.4, 95.7, 94.8, 84.3, 81.8, 80.8, 80.3, 79.2, 79.0, 78.3, 74.8, 72.6, 68.4, 68.3 (*2), 67.6, 67.5, 67.1, 57.0, 56.6, 45.6, 40.4, 39.7, 36.6, 35.2, 35.1, 34.4, 34.2, 31.1, 30.5, 27.5, 20.2, 19.9, 18.3, 17.9, 16.3, 15.1, 12.9, 12.0

EXAMPLE 24

Preparation of Compound 24

Compound 14 (0.10 g) was dissolved in dichloromethane (1.0 mL), imidazole (30 mg), triphenylphosphine (60 mg) and iodine (30 mg) were added to the solution, and the mixture was stirred at room temperature for 4 hours. Excess iodine was reduced with a saturated aqueous sodium sulfite solution, and then the mixture was extracted with dichloromethane. The collected dichloromethane layer was washed with saturated brine and dried over anhydrous sodium sulfate. The solvent was evaporated under reduced pressure to give a crude product. The resulting crude product was purified by column chromatography on silica gel with eluting solvents of hexane/ethyl acetate=5/1 to give 83 mg of the desired substance (yield: 75%).

IR(KBr) $\lambda_{max}$(cm$^{-1}$): 3455, 2962, 2933, 1743, 1458, 1387, 1338, 1309, 1252, 1203, 1161, 1124, 1084, 1055, 984

$^1$H NMR (270 MHz, CDCl$_3$, partial data) δ (ppm): 5.67 (4H, m), 5.50 (1H, dd, J=2.3, 9.9 Hz), 5.47 (1H, br.d, J=1.7 Hz), 5.30 (1H, d, J=3.0 Hz), 5.12 (1H, m), 4.93 (1H, m), 4.79 (1H, d, J=3.3 Hz), 4.66 (1H, d, J=14.4 Hz), 4.55 (1H, d, J=14.4 Hz), 4.36 (1H, m), 4.05 (1H, m), 3.96 (1H, br.s), 3.81 (1H, d, J=5.3 Hz), 3.40 (6H, s), 3.24 (3H, s), 3.21 (1H, t, J=9.1 Hz), 2.86 (1H, t, J=9.1 Hz), 2.57 (1H, m), 1.76 (3H, s), 1.28 (3H, d, J=5.9 Hz), 1.23 (3H, d, J=5.9 Hz), 1.16 (3H, d, J=6.9 Hz), 0.91 (9H, s), 0.12 (15H, s)

$^{13}$C NMR (67.8 MHz, CDCl$_3$) δ (ppm): 170.4, 140.4, 136.7, 135.8, 135.1, 134.4, 130.0, 125.0, 120.7, 120.5, 118.5, 98.3, 95.7, 94.9, 84.7, 83.8, 81.7, 80.7, 80.6, 79.1, 78.3, 74.7, 73.3, 69.5, 68.3, 68.0, 67.5 (*2), 67.1, 56.9, 56.4, 47.2, 40.9, 39.7, 36.1, 35.2, 35.1, 34.4, 34.2, 30.4, 27.4, 25.8 (*3), 20.1, 20.0, 18.4 (*2), 18.0, 16.4, 15.0, 12.9, 12.0, 3.7, 2.4 (*3), −4.5, −4.8

EXAMPLE 25

Preparation of Compound 25

Compound 24 (87 mg) was dissolved in tetrahydrofuran (0.10 mL), Solution A (0.10 mL) was added to the solution, and the mixture was stirred overnight at room temperature. Then, the reaction mixture was treated and purified in the manners similar to those in Example 2 to give 0.74 g of the desired compound (yield: 100%).

HR-FAB-MS: calcd for $C_{50}H_{75}O_{14}I$ [M+Na]$^+$ 1049.4099 found 1049.4099

IR(KBr) $\lambda_{max}$(cm$^{-1}$): 3462, 2966, 2933, 1714, 1454, 1380, 1340, 1300, 1263, 1194, 1161, 1120, 1053, 985

$^1$H NMR (270 MHz, CDCl$_3$, partial data) δ (ppm): 5.84 (1H, m), 5.73 (3H, m), 5.53 (1H, dd, J=2.0, 9.7 Hz), 5.40 (1H, br.s), 5.35 (1H, m), 5.31 (1H, d, J=3.3 Hz), 4.97 (1H, m), 4.75 (1H, d, J=3.3 Hz), 4.66 (2H, s), 4.27 (1H, m), 4.05 (1H, m), 3.94 (1H, d, J=6.3 Hz), 3.91 (1H, br.s), 3.41 (6H, s), 3.27 (1H, d, J=2.3 Hz), 3.23 (2H, m), 3.18 (1H, t, J=8.9 Hz), 2.86 (1H, t, J=8.9 Hz), 2.50 (1H, m), 2.00 (1H, m), 1.85 (3H, s), 1.76 (1H, m), 1.47 (3H, s), 1.27 (3H, d, J=6.3 Hz), 1.22 (3H, d, J=6.3 Hz), 1.14 (3H, d, J=6.6 Hz)

$^{13}$C NMR (67.8 MHz, CDCl$_3$) δ (ppm): 173.6, 139.5, 138.0, 137.9, 136.2, 135.1, 127.7, 124.7, 120.3, 118.2, 117.9, 98.3, 95.7, 94.8, 84.6, 81.8, 80.7, 80.3, 79.2, 79.0, 78.2, 74.8, 73.2, 68.3 (*3), 67.6, 67.4, 67.1, 56.9, 56.5, 45.6, 40.4, 39.7, 36.5, 35.1 (*2), 34.4, 34.2, 30.5, 27.4, 20.1, 19.9, 18.3, 18.0, 16.3, 15.0, 12.9, 12.0, 3.7

EXAMPLE 26

Preparation of Compound 26

Compound 21 (80 mg) was dissolved in dichloromethane (0.90 mL), acetic anhydride (86 µl) was added to the solution, and the mixture was stirred at room temperature for 3 hours. A saturated aqueous sodium hydrogencarbonate solution was added to the mixture, and then the mixture was extracted with dichloromethane. The collected dichloromethane layer was washed with saturated brine and dried over anhydrous sodium sulfate. The solvent was evaporated under reduced pressure to give a crude product.

The resulting crude product was dissolved in tetrahydrofuran (0.10 mL), Solution A (0.10 mL) was added to the solution, and the mixture was stirred overnight at room temperature. Then, the mixture was treated in the manner similar to that in Example 2. The resulting product was purified by column chromatography on silica gel with eluting solvents of chloroform/methanol=50/1 to give 46 mg of the desired compound (yield: 66%).

HR-FAB-MS: calcd for $C_{52}H_{79}O_{15}N$ [M+Na]$^+$ 980.5347 found 980.5342

IR(KBr) $\lambda_{max}$(cm$^{-1}$): 3455, 2968, 2933, 1724, 1716, 1660, 1549, 1454, 1381, 1340, 1290, 1194, 1161, 1120, 1053, 987

$^1$H NMR (270 MHz, CDCl$_3$, partial data) δ (ppm): 6.74 (1H, br.s), 5.82 (1H, m), 5.73 (3H, m), 5.53 (1H, dd, J=2.3, 9.7 Hz), 5.40 (1H, br.s), 5.38 (1H, m), 5.35 (1H, d, J=3.3 Hz), 4.95 (1H, m), 4.74 (1H, d, J=3.3 Hz), 4.66 (2H, s), 4.26 (1H, m), 3.94 (1H, d, J=6.3 Hz), 3.91 (1H, br.s), 3.42 (6H, s), 3.27 (1H, d, J=2.0 Hz), 3.20 (1H, t, J=9.1 Hz), 2.87 (1H, t, J=9.2 Hz), 2.50 (1H, m), 2.00 (1H, m), 1.97 (3H, s), 1.85 (3H, s), 1.73 (1H, m), 1.47 (3H, s), 1.23 (3H, d, J=5.9 Hz), 1.21 (3H, d, J=5.6 Hz), 1.13 (3H, d, J=6.9 Hz)

$^{13}$C NMR (67.8 MHz, CDCl$_3$) δ (ppm): 173.7, 170.0, 139.6, 137.9 (*2), 136.2, 135.1, 127.7, 124.7, 120.3, 118.2, 117.9, 98.1, 95.7, 94.9, 85.3, 81.9, 80.4, 80.3, 79.3, 79.1, 77.9, 74.8, 72.0, 68.4, 68.3 (*2), 67.8, 67.6, 67.1, 56.4, 56.2, 45.6, 40.4, 40.2, 39.7, 36.6, 35.1, 34.8, 34.4, 34.2, 30.5, 27.4, 23.1, 20.1, 19.9, 18.3, 17.9, 16.3, 15.1, 12.9, 12.0

EXAMPLE 27

Preparation of Compound 27

Compound 23 (50 mg) was dissolved in dimethyl sulfoxide (0.50 mL), piperidine (11 µl) was added to the solution, and the mixture was stirred at 40° C. for 1 hour. Purified water was added to the mixture, and then the mixture was extracted with ethyl acetate. The collected ethyl acetate layer was washed with water and dried over anhydrous magnesium sulfate. The solvent was evaporated under reduced pressure to give a crude product. The resulting crude product was purified by column chromatography on silica gel with eluting solvents of chloroform/methanol=30/1 to give 37 mg of the desired substance (yield: 73%). As chloroform for the eluting solvent, ten drops of 30% aqueous ammonia was added dropwise to 100 mL of chloroform and used.

HR-FAB-MS: calcd for $C_{54}H_{85}O_{14}N_2$ [M+H]$^+$ 984.6048 found 984.6053

IR(KBr) $\lambda_{max}$(cm$^{-1}$): 3450, 2966, 2933, 1736, 1718, 1452, 1383, 1342, 1309, 1271, 1196, 1161, 1122, 1053, 985

$^1$H NMR (270 MHz, CDCl$_3$, partial data) δ (ppm): 5.85 (1H, m), 5.73 (3H, m), 5.53 (1 dd, J=2.0, 9.9 Hz), 5.40 (1H, br.s), 5.38 (1H, m), 5.29 (1H, d, J=3.0 Hz), 4.96 (1H, m), 4.75 (1H, d, J=3.3 Hz), 4.67 (2H, s), 4.27 (1H, br.d, J=5.7 Hz), 4.01 (1H, br.s), 3.95 (1H, d, J=5.9 Hz), 3.42 (6H, s), 3.28 (1H, d, J=2.0 Hz), 3.18 (1H, t, J=8.9 Hz), 2.82 (1H, t, J=8.9 Hz), 2.60 (2H, t, J=5.9 Hz), 2.50 (5H, m), 2.00 (1H, m), 1.85 (3H, s), 1.76 (1H, m), 1.47 (3H, s), 1.23 (3H, d, J=5.6 Hz), 1.21 (3H, d, J=5.3 Hz), 1.14 (3H, d, J=6.9 Hz)

$^{13}$C NMR (67.8 MHz, CDCl$_3$) δ (ppm): 173.6, 139.6, 138.0, 137.9, 136.2, 135.1, 127.7, 124.7, 120.3, 118.2, 118.0, 98.5, 95.7, 94.9, 84.9, 81.8, 80.8, 80.3, 79.2, 79.1, 78.2, 74.8, 69.8, 68.4, 68.3 (*2), 67.7, 67.6, 67.2, 58.7, 57.1, 56.6, 54.6 (*2), 45.7, 40.4, 39.7, 36.6, 35.3, 35.1, 34.4, 34.2, 30.5, 27.5, 25.4 (*2), 24.0, 20.1, 19.9, 18.3, 17.9, 16.3, 15.0, 12.9, 12.0

EXAMPLE 28

Preparation of Compound 28

Compound 23 (50 mg) was dissolved in dimethyl sulfoxide (0.50 mL), morpholine (5.0 µl) was added to the solution, and the mixture was stirred at 40° C. for 2 hours. Purified water was added to the mixture, and then the mixture was extracted with ethyl acetate. The collected ethyl acetate layer was washed with water and dried over anhydrous magnesium sulfate. The solvent was evaporated under reduced pressure to give a crude product. The resulting crude product was purified by column chromatography on silica gel with eluting solvents of chloroform/methanol=30/1 to give 50 mg of the desired substance (yield: 100%). As chloroform for the eluting solvent, ten drops of 30% aqueous ammonia was added dropwise to 100 mL of chloroform and used.

HR-FAB-MS: calcd for $C_{54}H_{84}O_{15}N$ [M]$^+$ 986.5841 found 986.5848

IR(KBr) $\lambda_{max}$(cm$^{-1}$): 3469, 2966, 2933, 1736, 1452, 1381, 1340, 1309, 1248, 1159, 1122, 1053, 985

$^1$H NMR (270 MHz, CDCl$_3$, partial data) δ (ppm): 5.84 (1H, m), 5.73 (3H, m), 5.52 (1 dd, J=2.3, 9.9 Hz), 5.40 (1H, br.s), 5.37 (1H, m), 5.29 (1H, d, J=3.3 Hz), 4.97 (1H, m), 4.74 (1H, d, J=3.3 Hz), 4.66 (2H, s), 4.27 (1H, br.s), 4.01 (1H, s), 3.98 (1H, d, J=6.3 Hz), 3.91 (1H, br.s), 3.75 (4H, br.s), 3.41 (6H, s), 3.27 (1H, d, J=1.9 Hz), 3.18 (1H, t, J=8.9 Hz), 2.81 (1H, t, J=9.1 Hz), 2.63 (2H, br.s), 2.59 (4H, br.s), 2.18 (1H, m), 2.00 (1H, m), 1.85 (3H, s), 1.76 (1H, m), 1.47 (3H, s), 1.23 (3H, d, J=5.6 Hz), 1.21 (3H, d, J=5.6 Hz), 1.14 (3H, d, J=6.9 Hz)

$^{13}$C NMR (67.8 MHz, CDCl$_3$) δ (ppm): 173.6, 139.6, 138.0, 137.9, 136.2, 135.1, 127.7, 124.7, 120.3, 118.2, 118.0, 98.4, 95.7, 94.8, 84.9, 81.8, 80.9, 80.3, 79.2, 79.1, 78.2, 74.8, 68.4, 68.3 (*3), 67.6, 67.5, 67.2, 66.5 (*2), 58.5, 56.9, 56.6, 53.6 (*2), 45.6, 40.4, 39.7, 36.5, 35.2, 35.1, 34.4, 34.2, 30.5, 27.4, 20.1, 19.9, 18.3, 17.8, 16.3, 15.0, 12.9, 12.0

EXAMPLE 29

Preparation of Compound 29

Compound 23 (50 mg) was dissolved in dimethyl sulfoxide (0.50 mL), piperazine (5.2 mg) was added to the solution, and the mixture was stirred at 40° C. for 2 hours. Purified water was added to the mixture, and then the mixture was extracted with ethyl acetate. The collected ethyl acetate layer was washed with water and dried over anhydrous magnesium sulfate. The solvent was evaporated under reduced pressure to give a crude product. The resulting crude product was purified by column chromatography on silica gel with eluting solvents of chloroform/methanol 30/1 to give 39 mg of the desired substance (yield: 78%). As chloroform for the eluting solvent, ten drops of 30% aqueous ammonia was added dropwise to 100 mL of chloroform and used.

HR-FAB-MS: calcd for $C_{54}H_{85}O_{14}N_2$ [M+H]$^+$ 985.6001 found 985.6019

IR(KBr) $\lambda_{max}$(cm$^{-1}$): 3452, 2966, 2933, 1738, 1716, 1454, 1385, 1342, 1309, 1263, 1193, 1159, 1122, 1053, 985

$^1$H NMR (270 MHz, CDCl$_3$, partial data) δ (ppm): 5.84 (1H, m), 5.73 (3H, m), 5.53 (1 dd, J=2.3, 9.9 Hz), 5.39 (1H, br.s), 5.36 (1H, m), 5.28 (1H, d, J=3.0 Hz), 4.96 (1H, m), 4.75 (1H, d, J=3.0 Hz), 4.66 (2H, s), 4.27 (1H, br.d, J=6.0 Hz), 3.95 (1H, br.s), 3.92 (1H, d, J=6.0 Hz), 3.41 (6H, s), 3.27 (1H, d, J=2.9 Hz), 3.18 (1H, t, J=8.9 Hz), 2.93 (4H, br.s), 2.80 (1H, t, J=8.9 Hz), 2.56 (7H, m), 2.00 (1H, m), 1.85 (3H, s), 1.76 (1H, m), 1.47 (3H, s), 1.22 (3H, d, J=5.6 Hz), 1.21 (3H, d, J=5.9 Hz), 1.14 (3H, d, J=6.9 Hz)

$^{13}$C NMR (67.8 MHz, CDCl$_3$) δ (ppm): 173.6, 139.6, 138.0, 137.9, 136.2, 135.1, 127.7, 124.7, 120.3, 118.2, 118.0, 98.5, 95.7, 94.8, 84.9, 81.8, 80.9, 80.3, 79.2, 79.1, 78.3, 74.8, 69.9, 68.3 (*2), 67.6, 67.5, 67.4, 67.2, 58.6, 57.1, 56.6, 53.7 (*2), 45.7, 45.3 (*2), 40.4, 39.7, 36.5, 35.3, 35.1, 34.4, 34.2, 30.5, 27.4, 20.1, 19.9, 18.3, 17.8, 16.3, 15.0, 12.9, 12.0

EXAMPLE 30

Preparation of Compound 30

5-O-tert-Butyldimethylsilyl-7-O-trimethylsilylayermectin B1a (0.50 g) was dissolved in dichloromethane (4.0 ml), rhodium(II) diacetate (2.0 mg) was added to the solution, then a solution of diethyl diazomalonate (0.44 g) in dichloromethane (1.0 mL) prepared in the manner similar to that of the preparation of the solution of ethyl diazoacetate in dichloromethane used in Example 1 was slowly added dropwise to the mixture, and the mixture was stirred at room temperature for 3 hours. A saturated aqueous sodium hydrogencarbonate solution was added to the mixture, and then the mixture was extracted with dichloromethane. The collected dichloromethane layer was washed with saturated brine and dried over anhydrous sodium sulfate. The solvent was evaporated under reduced pressure to give a crude product. The resulting crude product was purified by column chromatography on silica gel using stepwise elution with eluting solvents of hexane/ethyl acetate=10/1 and 5/1 to give 0.20 g of the desired substance (yield: 34%).

HR-FAB-MS: calcd for $C_{64}H_{104}O_{18}Si_2$ [M+Na]$^+$ 1239.6659 found 1239.6641

IR(KBr) $\lambda_{max}$(cm$^{-1}$): 3469, 2962, 2933, 1768, 1743, 1464, 1387, 1336, 1308, 1252, 1205, 1161, 1126, 1053, 985

$^1$H NMR (270 MHz, CDCl$_3$, partial data) δ (ppm): 5.76 (3H, m), 5.64 (1H, dt, J=9.2, 14.2 Hz), 5.51 (1H, dd, J=2.3, 10.2 Hz), 5.48 (1H, br.d, J=1.7 Hz), 5.29 (1H, d, J=3.3 Hz), 5.10 (1H, m), 4.94 (1H, m), 4.88 (1H, s), 4.80 (1H, d, J=3.3 Hz), 4.67 (1H, d, J=15.0 Hz), 4.56 (1H, d, J=15.0 Hz), 4.38 (1H, m), 4.26 (4H, m), 3.97 (1H, br.s), 3.82 (1H, d, J=5.3 Hz), 3.41 (3H, s), 3.27 (1H, d, J=2.6 Hz), 3.25 (3H, s), 3.21 (1H, t, J=8.9 Hz), 3.06 (1H, t, J=8.9 Hz), 2.58 (1H, m), 1.77 (3H, s), 1.51 (3H, s), 1.28 (12H, m), 1.18 (3H, d, J=6.9 Hz), 0.93 (9H, s), 0.13 (15H, s)

$^{13}$C NMR (67.8 MHz, CDCl$_3$) δ (ppm): 170.5, 167.2, 167.0, 140.4, 136.7, 135.9, 135.2, 134.4, 128.0, 125.0, 120.8, 120.6, 118.5, 98.5, 95.8, 94.8, 85.7, 83.8, 81.6, 81.3, 80.8, 80.7, 79.1, 78.2, 74.8, 69.5, 68.3, 68.0, 67.5, 67.0 (*2), 61.8, 61.5, 56.4, 55.4, 47.2, 40.9, 39.8, 36.2, 35.3, 34.5, 34.4, 34.3, 30.5, 27.5, 25.9 (*3), 20.2, 20.1, 18.4 (*2), 17.8, 16.4, 15.0, 14.1, 14.0, 12.1, 2.4 (*3), −4.5, −4.8

EXAMPLE 31

Preparation of Compound 31

Compound 30 (0.10 g) was dissolved in tetrahydrofuran (1.0 mL), Solution A (0.10 mL) was added to the solution, and the mixture was stirred at room temperature for 3 hours. Then, the reaction mixture was treated and purified in the manners similar to those in Example 2 to give 0.46 g of the desired compound (yield: 54%).

HR-FAB-MS: calcd for C$_{50}$H$_{75}$O$_{14}$I [M+Na]$^+$ 1049.4099 found 1049.4099

IR(KBr) λ$_{max}$(cm$^{-1}$): 3462, 2966, 2933, 1714, 1454, 1380, 1340, 1300, 1263, 1194, 1161, 1120, 1053, 985

$^1$H NMR (270 MHz, CDCl$_3$, partial data) δ (ppm): 5.85 (1H, m), 5.74 (3H, m), 5.54 (1 dd, J=2.3, 9.9 Hz), 5.41 (1H, br.s), 5.39 (1H, m), 5.31 (1H, d, J=3.3 Hz), 4.97 (1H, m), 4.88 (1H, s), 4.76 (1H, d, J=3.3 Hz), 4.68 (2H, s), 4.26 (5H, m), 3.96 (1H, d, J=6.3 Hz), 3.93 (1H, br.s), 3.42 (3H, s), 3.28 (1H, d, J=2.0 Hz), 3.26 (3H, s), 3.18 (1H, t, J=8.9 Hz), 3.06 (1H, t, J=9.1 Hz), 2.52 (1H, m), 2.01 (1H, m), 1.86 (3H, s), 1.77 (1H, m), 1.48 (3H, s), 1.27 (12H, m), 1.16 (3H, d, J=6.9 Hz)

$^{13}$C NMR (67.8 MHz, CDCl$_3$) δ (ppm): 173.7, 167.1, 167.0, 139.6, 138.1, 138.0, 136.2, 135.1, 127.8, 124.7, 120.4, 118.3, 118.0, 98.5, 95.8, 94.7, 85.7, 81.7, 81.2, 80.8, 80.4, 79.3, 79.1, 78.2, 74.9, 68.4, 68.3 (*2), 67.7, 67.2, 66.8, 61.8, 61.5, 56.5, 55.5, 45.7, 40.5, 39.8, 36.6, 35.1, 34.5, 34.4, 34.2, 30.5, 27.7, 20.2, 19.8, 18.4, 17.8, 16.4, 15.1, 14.1, 14.0, 12.9, 12.0

EXAMPLE 32

Preparation of Compound 35

Under nitrogen atmosphere, 5-O-tert-butyldimethylsilyl-7-O-trimethylsilylivermectin (0.10 g) obtained in Reference Example 3 was dissolved in dichloromethane (0.20 mL), diacetylrhodium dimer (1.0 mg) was added to the solution, and the mixture was stirred at room temperature for 10 minutes. Then, a solution of ethyl diazoacetate (22 μl) in dichloromethane (0.20 mL) was slowly added dropwise to the mixture, and the mixture was stirred at room temperature for 5.5 hours. A saturated aqueous sodium hydrogencarbonate solution was added to the mixture, and then the mixture was extracted with dichloromethane. The collected dichloromethane layer was washed with saturated brine and dried over anhydrous magnesium sulfate. The solvent was evaporated under reduced pressure to give a crude product. The resulting crude product was is purified by column chromatography on silica gel using stepwise elution with eluting solvents of hexane/ethyl acetate=5/1 and 2/1 to give 0.59 g of the desired substance (yield: 55%).

IR(KBr) λ$_{max}$(cm$^{-1}$): 3450, 2960, 2933, 1743, 1456, 1387, 1338, 1308, 1252, 1201, 1169, 1128, 1101, 1055, 985

$^1$H NMR (270 MHz, CDCl$_3$, partial data) δ (ppm): 5.70 (3H, m), 5.47 (1H, br.s), 5.30 (1H, d, J=2.6 Hz), 5.12 (1H, m), 4.86 (1H, m), 4.81 (1H, d, J=3.0 Hz), 4.66 (1H, d, J=14.2 Hz), 4.56 (1H, d, J=14.2 Hz), 4.36 (1H, m), 4.36 (1H, d, J=3.6 Hz), 4.21 (2H, q, J=7.1 Hz), 3.97 (1H, br.s), 3.81 (1H, d, J=5.3 Hz), 3.40 (3H, s), 3.35 (3H, s), 3.24 (1H, m), 3.21 (1H, t, J=8.6 Hz), 2.95 (1H, t, J=8.9 Hz), 2.58 (1H, m), 2.29 (5H, m), 1.77 (3H, s), 1.51 (3H, s), 1.31 (3H, d, J=5.9 Hz), 1.28 (3H, t, J=7.1 Hz), 1.27 (3H, d, J=6.9 Hz), 1.17 (3H, d, J=6.9 Hz), 0.93 (9H, s), 0.13 (15H, s)

$^{13}$C NMR (67.8 MHz, CDCl$_3$) δ (ppm): 170.7, 170.5, 140.4, 136.8, 135.1, 134.3, 124.9, 120.8, 120.5, 118.8, 98.3, 97.5, 94.8, 84.8, 83.6, 81.5, 80.9, 80.7, 79.1, 78.7, 70.0, 69.5, 68.8, 67.4, 67.3, 67.2, 67.1, 60.6, 56.3, 56.2, 47.2, 41.8, 39.6, 36.4, 35.6, 35.5, 34.8, 34.3, 34.1, 31.2, 28.0, 27.1, 25.8 (*3), 20.1, 20.0, 18.4 (*2), 17.9, 17.4, 15.0, 14.2, 12.3, 11.9, 2.3 (*3), −4.5, −4.7

EXAMPLE 33

Preparation of Compound 36

Compound 35 (50 mg) was dissolved in tetrahydrofuran (500 μl), Solution A (50 μl) was added to the solution, and the mixture was stirred overnight at room temperature. Then, the reaction mixture was treated and purified in the manners similar to those in Example 2 to give 47 mg of the desired compound (yield: 100%).

HR-FAB-MS: calcd for C$_{52}$H$_{80}$O$_{16}$ [M+Na]$^+$ 983.5344 found 983.5338

IR(KBr) λ max(cm$^{-1}$): 3481, 2964, 2931, 1758, 1737, 1456, 1379, 1340, 1300, 1273, 1198, 1172, 1122, 1101, 1053, 987

$^1$H NMR (270 MHz, CDCl$_3$, partial data) δ (ppm): 5.86 (1H, m), 5.75 (2H, m), 5.42 (1 br.s), 5.35 (1H, m), 5.32 (1H, d, J=3.3 Hz), 4.97 (1H, m), 4.77 (1H, d, J=3.0 Hz), 4.68 (2H, br.s), 4.37 (1H, d, J=4.0 Hz), 4.29 (1H, m), 4.21 (2H, q, J=7.1 Hz), 4.11 (1H, br.s), 3.97 (1H, d, J=6.3 Hz), 3.93 (1H, br.s), 3.81 (2H, m), 3.64 (3H, m), 3.42 (3H, s), 3.36 (3H, s), 3.28 (1H, q, J=2.3 Hz), 3.20 (1H, t, J=9.0 Hz), 2.95 (1H, t, J=8.9 Hz), 2.52 (1H, m), 2.26 (5H, m), 1.97 (1H, m), 1.87 (3H, s), 1.49 (3H, s), 1.31 (3H, d, J=5.9 Hz), 1.28 (3H, t, J=7.1 Hz), 1.24 (3H, d, J=6.3 Hz), 1.13 (3H, d, J=6.9 Hz)

$^{13}$C NMR (67.8 MHz, CDCl$_3$) δ (ppm): 173.8, 170.5, 139.6, 138.0, 137.9, 134.9, 124.6, 120.4, 120.0, 118.0, 98.3, 97.4, 94.6, 84.7, 81.6, 80.8, 80.3, 79.2, 79.0, 78.5, 76.6, 70.0 (β2), 68.6, 68.4, 67.6, 67.1 (*2), 60.6, 56.5, 56.2, 45.6, 41.1, 39.7, 36.9, 35.7, 35.4, 34.8, 34.4, 34.0, 31.2, 28.0, 27.2, 20.2, 19.9, 18.3, 17.9, 17.4, 15.1, 14.2, 12.4, 12.0

EXAMPLE 34

Preparation of Compound 39

Compound 35 (500 mg, 436 mmol) was dissolved in tetrahydrofuran (4.5 mL), a 1 mol/L aqueous potassium hydroxide solution (650 μL) was added to the solution, and the mixture was stirred at room temperature for 18 hours. A saturated aqueous ammonium chloride solution (5 mL) was added to the mixture for neutralization, and the mixture was extracted 3 times with ethyl acetate (5 mL). The collected ethyl acetate layers were washed with a saturated aqueous ammonium chloride solution (5 mL) and saturated brine (5 mL) and dried over anhydrous sodium sulfate. The solvent was evaporated under reduced pressure to give a crude product. The crude product was treated and purified in the manners similar to those in Example 2 to give 198 mg of the desired compound (yield: 49%, for the two steps).

HR-FAB-MS: calcd for $C_{50}H_{75}O_{16}$ [M+2Na]$^+$ 977.4851 found 977.4877 IR(KBr) $\lambda_{max}$(cm$^{-1}$): 3465, 2966, 2933, 1763, 1735, 1456, 1379, 1342, 1309, 1273, 1244, 1200, 1171, 1122, 1055, 985

EXAMPLE 35

Preparation of Compound 37

Under nitrogen atmosphere, a 1.0 mol/L solution of super hydride in tetrahydrofuran (12.6 mL, 12.9 mmol) was added dropwise to a solution of Compound 35 (2.48 g, 2.16 mmol) in tetrahydrofuran (21 mL) at −78° C., and the mixture was stirred at the same temperature for 2 hours. After a 30% aqueous hydrogen peroxide solution (1.6 mL) was added to the mixture, the mixture was stirred at the same temperature for 30 minutes. Sodium sulfite (100 mg) was added to the mixture, and the mixture was extracted 3 times with ethyl acetate (30 mL). The collected ethyl acetate layers were washed with saturated brine (10 mL) and dried over anhydrous sodium sulfate. The solvent was evaporated under reduced pressure to give a crude product. The resulting crude product was purified by chromatography on silica gel (150 g) with eluting solvents of hexane/ethyl acetate=3/1 to give 1.59 g of the desired compound (yield: 67%).

HR-FAB-MS: calcd for $C_{61}H_{102}O_{16}Si_2$ [M+Na]$^+$ 1127.6498, found 1127.6484

IR(KBr) $\lambda_{max}$(cm$^{-1}$): 3461, 2960, 2931, 1743, 1461, 1387, 1336, 1309, 1252, 1203, 1168, 1124, 1105, 1055, 1009, 985

EXAMPLE 36

Preparation of Compound 40

Compound 37 (90.0 mg, 81.4 µmol) was treated and purified in the manners similar to those in Example 2 to give 65.7 mg of the desired compound (yield: 88%). HR-FAB-MS: calcd for $C_{50}H_{78}O_{15}$ [M+Na]$^+$ 941.5238, found 941.5229 IR(KBr) $\lambda_{max}$(cm$^{-1}$): 3459, 2964, 2933, 1738, 1456, 1379, 1340, 1308, 1245, 1198, 1171, 1120, 1054, 1011, 985

EXAMPLE 37

Preparation of Compound 38

Under nitrogen atmosphere, triphenylphosphine (473 mg, 1.79 mmol), imidazole (491 mg, 7.19 mmol) and carbon tetrabromide (598 mg, 1.79 mmol) were added to a solution of Compound 37 (795 mg, 719 u mol) in dichloromethane (7.2 mL), and the mixture was stirred at room temperature for 2 hours. After a 30% aqueous hydrogen peroxide solution (1.6 mL) was added to the mixture, the mixture was stirred for 30 minutes at the same temperature. Sodium sulfite (100 mg) was added to the mixture, and the mixture was extracted 3 times with ethyl acetate (30 mL). The collected ethyl acetate layers were washed with saturated brine (10 mL) and dried over anhydrous sodium sulfate. The solvent was evaporated under reduced pressure to give a crude product. The resulting crude product was purified by chromatography on silica gel (150 g) with eluting solvents of hexane/ethyl acetate=5/1 to give 432 mg of the desired compound (yield: 51%).

HR-FAB-MS: calcd for $C_{59}H_{99}BrO_{14}Si_2$ [M+Na]$^+$ 1189.5654, found 1189.5674

IR(KBr) $\lambda_{max}$(cm$^{-1}$): 2960, 2931, 1743, 1461, 1387, 1336, 1309, 1252, 1203, 1168, 1124, 1105, 1055, 1009, 985

EXAMPLE 38

Preparation of Compound 41

Compound 38 (126 mg, 107 µmol) was treated and purified in the manners similar to those in Example 2 to give 67.2 mg of the desired compound (yield: 64%). HR-FAB-MS: calcd for $C_{50}H_{77}BrO_{14}$ [M+Na]$^+$ 1003.4394, found 1003.4411

IR(KBr) $\lambda_{max}$(cm$^{-1}$): 3455, 2964, 2931, 1731, 1717, 1456, 1379, 1340, 1308, 1274, 1243, 1196, 1171, 1120, 1053, 985

EXAMPLE 39

Preparation of Compound 42

Reactions were performed, and the product was treated and purified in the manners similar to those in Example 1 by using 5-O-tert-butyldimethylsilyl-7-O-trimethylsilylayermectin B2a (100 mg, 92.8 µmol) obtained in Reference Example 5 to give 32.3 mg of the desired compound (yield: 30%).

IR(KBr) $\lambda_{max}$(cm$^{-1}$): 3531, 2962, 2933, 1743, 1462, 1387, 1336, 1296, 1252, 1203, 1167, 1126, 1099, 1053, 984

EXAMPLE 40

Preparation of Compound 43

Compound 42 (32.3 mg, 27.3 µmol) was treated and purified in the manners similar to those in Example 2 to give 19.1 mg of the desired compound (yield: 70%).

HR-FAB-MS: calcd for $C_{52}H_{80}O_{17}$ [M+Na]$^+$ 999.5293, found 999.5289

IR(KBr) $\lambda_{max}$(cm$^{-1}$): 3525, 2967, 2933, 1759, 1737, 1452, 1387, 1340, 1300, 1263, 1198, 1169, 1124, 1084, 1053, 985

EXAMPLE 41

Preparation of Compound 44

Under nitrogen atmosphere, dimethyl sulfoxide (30 µl) was added to a solution of oxalyl chloride (20 µl, 214 µmol) in dichloromethane (200 µl) at −78° C., and the mixture was stirred for 5 minutes. Then, Compound 42 (50.0 mg, 42.9 µmol) and a solution of triethylamine (60 µl) in dichloromethane (700 µl) were added dropwise to the mixture, and the mixture was warmed to 0° C. and further stirred for 3 hours. After a saturated aqueous ammonium chloride solution (5 mL) was added to the reaction solution, the mixture was extracted 3 times with dichloromethane (10 mL), and the organic layer was dried over anhydrous sodium sulfate. The solvent was evaporated under reduced pressure to give a crude product. The resulting crude product was purified by chromatography on silica gel (250 mg) with eluting solvents of hexane/ethyl acetate=3/1 to give 41.5 mg of the desired compound (yield: 83%).

HR-FAB-MS: calcd for $C_{81}H_{100}O_{17}Si_2$ [M+Na]$^+$ 1183.6397, found 1183.6405

IR(KBr) $\lambda_{max}$(cm$^{-1}$): 3450, 2962, 2935, 1743, 1726, 1456, 1387, 1335, 1296, 1252, 1200, 1167, 1128, 1099, 1062, 985

EXAMPLE 42

Preparation of Compound 45

Compound 44 (41.5 mg, 35.7 μmol) was treated and purified in the manners similar to those in Example to give 31.5 mg of the desired compound (yield: 91%).

HR-FAB-MS: calcd for $C_{52}H_{78}O_{17}$ [M+Na]$^+$ 997.5137, found 997.5148

IR(KBr) $\lambda_{max}$(cm$^{-1}$): 3483, 2975, 2935, 1757, 1724, 1452, 1385, 1340, 1298, 1238, 1200, 1169, 1124, 1101, 1055, 985

EXAMPLE 43

Preparation of Compound 46

To a solution of Compound 44 (50.3 mg, 43.3 μmol) in a mixed solvent of methanol (1 mL) and purified water (140 μl), sodium acetate (14.2 mg, 173 μmol) and O-methylhydroxylamine hydrochloride (7.2 mg, 86.6 μmol) were added, and the mixture was stirred at room temperature for 3 hours. After a saturated aqueous sodium hydrogencarbonate solution (5 mL) was added to the reaction solution, the mixture was extracted with ethyl acetate (10 mL×3), and the organic layer was dried over anhydrous sodium sulfate. The solvent was evaporated under reduced pressure to give a crude product. The resulting crude product was purified by chromatography on silica gel (250 mg) with eluting solvents of chloroform/methanol=10/1 to give 48.1 mg of the desired compound (yield: 93%).

IR(KBr) $\lambda_{max}$(cm$^{-1}$): 3465, 2960, 2935, 1743, 1463, 1387, 1336, 1296, 1252, 1203, 1169, 1128, 1099, 1053, 991

EXAMPLE 44

Preparation of Compound 47

Compound 46 (48.1 mg, 40.3 μmol) was treated and purified in the manners similar to those in Example 2 to give 40.5 mg of the desired compound (yield: 100%).

HR-FAB-MS: calcd for $C_{53}H_{81}O_{17}$ [M+Na]$^+$ 1026.5402, found 1026.5430

IR(KBr) $\lambda_{max}$(cm$^{-1}$): 3483, 2972, 2935, 1759, 1735, 1452, 1383, 1340, 1298, 1198, 1173, 1124, 1101, 1051, 989

REFERENCE EXAMPLE 1

5-O-tert-Butyldimethylsilyl-7-O-trimethylsilylayermectin B1a

5-O-tert-Butyldimethylsilylayermectin B1a (4.9 g), which was known from literature (Journal of Medicinal Chemistry (J. Med. Chem.), vol. 25, 658–663 (1982), was dissolved in N,N-dimethylformamide (35 mL). Imidazole (2.4 mg) and trimethylsilyl chloride (2.2 mL) were added to the solution, and the mixture was stirred at room temperature for 6.5 hours. After purified water was added, the mixture was extracted with diethyl ether. The collected diethyl ether layer was washed with water and dried over anhydrous magnesium sulfate. The solvent was evaporated under reduced pressure to give a crude product. Then, the crude product was dissolved in tetrahydrofuran (110 mL), an aqueous acetic acid solution (acetic acid: 44 mL, purified water: 22 mL) was slowly added dropwise to the mixture, and the mixture was stirred at room temperature for 2.5 hours. A saturated aqueous sodium hydrogencarbonate solution was added to the mixture for neutralization, and then the mixture was extracted with ethyl acetate. The collected ethyl acetate layer was washed successively with a saturated aqueous sodium hydrogencarbonate solution and saturated brine and dried over anhydrous magnesium sulfate. The solvent was evaporated under reduced pressure to give a crude product. The resulting crude product was purified by column chromatography on silica gel using stepwise elution with eluting solvents of hexane/ethyl acetate=2/1 and 1/1 to give 3.9 g of the desired substance (yield: 75%).

$^1$H NMR (270 MHz, CDCl$_3$, partial data) 6 (ppm): 5.73 (3H, m), 5.63 (1H, dt, J=9.2, 14.2 Hz), 5.50 (1H, dd, J=2.0, 9.9 Hz), 5.48 (1H, br.s), 5.36 (1H, d, J=3.3 Hz), 5.10 (1H, m), 4.93 (1H, m), 4.79 (1H, d, J=3.3 Hz), 4.66 (1H, d, J=14.3 Hz), 4.55 (1H, d, J=14.3 Hz), 4.37 (1H, m), 3.96 (1H, br.s), 3.81 (1H, d, J=5.6 Hz), 3.41 (3H, s), 3.39 (3H, s), 3.26 (1H, d, J=2.3 Hz), 3.25 (1H, t, J=9.2 Hz), 3.15 (1H, t, J=9.2 Hz), 2.57 (1H, m), 1.76 (3H, s), 1.50 (3H, s), 1.26 (3H, d, J=6.3 Hz), 1.25 (3H, d, J=5.9 Hz), 1.17 (3H, d, J=6.9 Hz), 0.92 (9H, s), 0.12 (15H, s)

$^{13}$C NMR (67.8 MHz, CDCl$_3$) δ (ppm): 170.5, 140.4, 136.6, 135.8, 135.2, 134.4, 128.0, 125.0, 120.7, 120.5, 118.5, 98.3, 95.8, 95.0, 83.6, 81.7, 80.6, 80.3, 79.2, 78.1, 76.0, 74.7, 69.5, 68.3, 68.1, 68.0, 67.5, 67.1, 56.3 (*2), 51.2, 47.2, 40.9, 39.7, 36.1, 35.2, 34.4, 34.2, 34.1, 30.4, 27.4, 25.8 (*3), 20.1, 20.0, 18.4 (*2), 17.6, 16.4, 15.0, 12.9, 12.0, 2.3 (*3), −4.5, −4.8

REFERENCE EXAMPLE 2

5-O-tert-Butyldimethylsilylivermectin

Ivermectin (2.2 g) was dissolved in N,N-dimethylformamide (25 mL), imidazole (680 mg) and tert-butyldimethylchlorosilane (750 mg) were added to the solution, and the mixture was stirred at room temperature for 3 hours. After an aqueous sodium hydrogencarbonate solution was added to the mixture, the mixture was extracted with The organic layer was dried over anhydrous magnesium sulfate, and the solvent was evaporated under reduced pressure to give a crude product. The resulting crude product was purified by column chromatography on silica gel with eluting solvents of dichloromethane/tetrahydrofuran=20/1 to give 1.6 g of the desired substance (yield: 63%).

HR-FAB-MS: calcd for $C_{54}H_{88}O_{14}Si$ [M+Na]$^+$ 1011.5841 found 1011.5873

IR(KBr) $\lambda_{max}$(cm$^{-1}$): 3450, 2963, 2931, 1714, 1635, 1456, 1381, 1254, 1120, 987

$^1$H NMR (270 MHz, CDCl$_3$, partial data) δ (ppm): 5.80 (1H, m), 5.71 (2H, m), 5.39 (1 d, J=3.3 Hz),5.31 (2H, m),4.98 (1H, m),4.77 (1H, d, J=3.0 Hz),4.68 (1H, d, J=16.2 Hz), 4.52 (1H, d, J=16.2 Hz), 4.22 (1H, m), 3.42 (6H, s), 1.78 (3H, s), 1.50 (3H, s), 1.27 (3H, d, J=6.3 Hz), 1.25 (3H, d, J=6.0 Hz), 1.15 (3H, d, J=6.9 Hz), 0.92 (9H, s), 0.13 (6H, s)

$^{13}$C NMR (67.8 MHz, CDCl$_3$) δ (ppm): 174.1, 141.2, 137.2 (*2), 135.0, 124.8, 119.3, 118.3, 117.2, 98.5, 97.5, 94.8, 81.8, 80.4, 80.2, 80.0, 79.3, 78.2, 77.5–76.5 (*1), 76.0, 69.5, 68.7, 68.1, 67.9, 67.2 (*2), 56.5, 56.4, 45.7, 41.1, 39.6, 36.8, 35.7, 35.4, 34.5, 34.1 (*2), 31.2, 28.1, 27.3, 25.8 (*3), 20.3, 20.0, 18.4, 17.6, 17.4, 15.2 (*2), 12.4, 12.1, −4.6, −4.9

REFERENCE EXAMPLE 3

5-O-tert-Butyldimethylsilyl-7-O-trimethylsilylivermectin

Under nitrogen atmosphere, 5-O-tert-butyldimethylsilylivermectin (8.6 g) obtained in Reference Example 2 was dissolved in N,N-dimethylformamide (87 mL). Imidazole (2.4 g) and trimethylsilyl chloride (3.8 mL) were successively added to the mixture, and the mixture was stirred at room temperature for 14 hours. Purified water was added to the mixture, and then the mixture was extracted with ethyl acetate. The collected ethyl acetate layer was washed with water and dried over anhydrous sodium sulfate. The solvent was evaporated under reduced pressure to give a crude product. Then, the crude product was dissolved in tetrahydrofuran (200 mL), an aqueous acetic acid solution (acetic acid: 80 mL, purified water: 40 mL) was slowly added dropwise to the mixture, and the mixture was stirred at room temperature for 4 hours. A saturated aqueous sodium hydrogencarbonate solution was added to the mixture for neutralization, and then the mixture was extracted with ethyl acetate. The collected ethyl acetate layer was washed successively with a saturated aqueous sodium hydrogencarbonate solution and saturated brine and dried over anhydrous magnesium sulfate. The solvent was evaporated under reduced pressure to give a crude product. The resulting crude product was purified by column chromatography on silica gel using stepwise elution with eluting solvents of hexane/ethyl acetate=4/1 and 3/1 to give 7.7 g of the desired substance (yield: 84%).

HR-FAB-MS: calcd for $C_{57}H_{96}O_{14}Si_2Na$ $[M+Na]^+$ 1083.6236 found 1083.6233

IR(KBr) $\lambda_{max}(cm^{-1})$: 3469, 2960, 2931, 1743, 1460, 1381, 1336, 1308, 1252, 1203, 1168, 1120, 1083, 1052, 987

$^1H$ NMR (270 MHz, $CDCl_3$, partial data) δ (ppm): 5.69 (3H, m), 5.47 (1H, br.s), 5.36 (1H, d, J=3.6 Hz), 5.12 (1H, m), 4.85 (1H, m), 4.80 (1H, d, J=3.6 Hz), 4.66 (1H, d, J=14.2 Hz), 4.55 (1H, d, J=14.2 Hz), 4.37 (1H, m), 3.97 (1H, br.s), 3.80 (1H, d, J=5.1 Hz), 3.39 (6H, s), 3.20 (3H, m), 2.57 (1H, m), 2.28 (5H, m), 1.77 (3H, s), 1.50 (3H, s), 1.26 (3H, d, J=6.2 Hz), 1.25 (3H, d, J=6.3 Hz), 1.17 (3H, d, J=6.6 Hz), 0.97 (9H, s), 0.12 (15H, s)

$^{13}C$ NMR (67.8 MHz, $CDCl_3$) δ (ppm): 170.7, 140.4, 136.7, 135.1, 134.3, 125.0, 120.8, 120.4, 118.8, 98.4, 97.5, 94.9, 83.6, 81.7, 80.7, 80.3, 79.2, 78.2, 76.6, 76.0, 69.5, 68.8, 68.1, 67.4, 67.2, 67.1, 56.3, 56.2, 47.2, 41.8, 39.6, 36.4, 35.6, 35.5, 34.4, 34.3, 34.1, 31.2, 28.1, 27.1, 25.8 (*3), 20.1, 20.0, 18.4 (*2), 17.6, 17.4, 15.0, 12.3, 11.9, 2.3 (*3), −4.5, −4.7

REFERENCE EXAMPLE 4

5-O-tert-Butyldimethylsilylayermectin B2a

Avermectin B2a (3.54 g, 3.97 mmol) was used as a starting material, and reactions were performed and the product was treated and purified in the manners similar to those in Reference Example 2 to give 1.90 g of the desired substance (yield: 48%).

HR-FAB-MS: calcd for $C_{54}H_{88}O_{15}Si$ $[M+Na]^+$ 1027.5790 found 1027.5763

IR(KBr) $\lambda_{max}(cm^{-1})$: 3533, 2962, 2933, 1714, 1462, 1385, 1338, 1304, 1255, 1196, 1167, 1124, 1082, 1051, 985

REFERENCE EXAMPLE 5

5-O-tert-Butyldimethylsilyl-7-O-trimethylsilylayermectin B2a

5-O-tert-Butyldimethylsilylayermectin B2a (1.00 g, 994 mmol) obtained in Reference Example 4 was used as a starting material, and reactions were performed and the product was treated and purified in the manners similar to those in Reference Example 3 to give 742 mg of the desired substance (yield: 69%).

HR-FAB-MS: calcd for $C_{57}H_{96}O_{15}Si_2$ $[M+Na]^+$ 1099.6185 found 1099.6207

IR(KBr) $\lambda_{max}(cm^{-1})$: 3529, 2962, 2933, 1745, 1462, 1387, 1336, 1304, 1252, 1187, 1169, 1126, 1084, 1053, 985

TEST EXAMPLE 1

Methods for determining antiparasitic effects of the compounds disclosed by the present invention are explained below.

As model insects for simple determination of antiparasitic and insecticidal activities, those insects are desired which can be easily obtained and bred in laboratories, and have no pathogenicity to a human. *Caenorhabditis elegans*, an unparasitic eelworm widely used in experiments of genetics, was used as a typical steam worm, and *artemia salina* used as feed for tropical fish and named Brine shrimp, was used instead of insects.

<Preparation of *Caenorhabditis elegans* Used for Evaluation>

*Escherichia. coli* for the feed of *caenorhabditis elegans* (mutant having uracil requirement) was inoculated in a seed medium for *E. coli* to which a small amount of uracil was added, and cultured with shaking at 27° C. for 1 day. A petri dish of 6 cm diameter was filled with 10 mL of an agar medium for eelworm proliferation, and the medium was solidified. Then 0.5 mL of the culture of *E. coli* was spread over the medium in the dish, and the dish was incubated at 37° C. to proliferate *E. coli* A piece of the agar was collected with a platinum loop from a petri dish in which *caenorhabditis elegans* successfully proliferated, and inoculated in petri dishes in which *E. coli* was proliferated. The petri dishes were incubated at 20° C. to proliferate *caenorhabditis elegans*. Since the life of eelworm is about 2 weeks, subculture was carried out every once a week. The eelworms grown with spread on the surface of the petri dish after 3 to 5 days from subculture were used for the experiments.

<Preparation of *artemia salina* Used for Evaluation>

To a buffer for *artemia salina* (obtained by dissolving 0.24% of Tris, 2.57% of sodium chloride, 0.47% of magnesium chloride, 0.07% of potassium chloride, 0.02% of sodium carbonate, 0.64% of magnesium sulfate and 0.11% of calcium chloride in distilled water and adjusting the pH to 7.1 with hydrochloric acid), dried eggs of *artemia salina* [Tetra Brine Shrimp Eggs, Warner Lambert Co.] were added. The noprius larvae 1 or 2 days after hatching were used for the experiments.

<Preparation of Agar Medium for Eelworm Proliferation>

Solution A was obtained by dissolving 0.3% of sodium chloride, 1.7% of bact-agar (DIFCO Co.), 0.5% of bact-peptone (DIFCO Co.) and 1.0% of yeast extract (DIFCO Co.) in distilled water.

Solution B was obtained by dissolving 0.5% of cholesterol in ethanol.

Solution C was obtained by dissolving 13.9% of calcium chloride in distilled water.

Solution D was obtained by dissolving 30.8% of magnesium sulfate heptahydrate in distilled water.

Solution E was obtained by dissolving 13.54% of $KH_2PO_4$ and 4.45% of $K_2HPO_4$ in distilled water.

The aforementioned Solutions A, C and D were sterilized in an autoclave at 121° C. for 20 minutes, and each solution was stored at 4° C.

The agar medium for eelworm proliferation was prepared by mixing the solutions in the following proportion: Solution A: 100 mL, Solution B: 0.1 mL, Solution C: 0.05 mL, Solution D: 0.1 mL and Solution E: 2.5 mL (without pH adjustment), and dispensing each 10 mL portion into petri dishes of 60×15 mm.

<Preparation of *E. coli* Seed Medium>

In distilled water, 2.0% of bact-trypton (DIFCO Co.), 0.55% of sodium chloride and 0.001% of uracil (SIGMA Co., pH 7.4) were dissolved, and the solution was sterilized in an autoclave at 121° C. for 20 minutes.

<Experimental Procedure>

Each well of a 96 well microplate was filled with the solution of the test compound (methanol as a solvent), and the solvent was removed using a vacuum pump, then 250 μl of the assay medium was added to each wells (the assay medium was prepared by dissolving 7.5 mM sodium hydrogencarbonate, 7.5 mM potassium chloride, 7.5 mM calcium chloride dihydrate and 7.5 mM magnesium sulfate heptahydrate in distilled water and adding 0.01% of lecithin to the solution), and then the microplate was shaken using a microplate mixer for 15 minutes. To each well, a few individuals of *caenorhabditis elegans* were added by softly rubbing the surface of the agar using a toothpick, or a few individuals of *artemia salina* were added together with 50 μgl of the buffer. The microplate was incubated at 20° C., and then the insects were observed after 24 and 48 hours under a microscope (magnification of 40×). The results were compared to those obtained without addition of the test compound, and evaluated by 4 grades.

The evaluation results were shown by indications of 4 grades from 0 to 3.

3: No movement

2: Between 1 and 3

1: A little week movements

0: Active movements

Of the 4 grades, Indications 3 and 2 were judged as effective, and Indications 1 and 0 as ineffective. The results are shown in Table 5. In Table 5, the values for each compound are minimum inhibitory concentrations (MIC) which were required to give Indication 2 (or 3) for *caenorhabditis elegans* or *artemia salina*. In Table 5, *caenorhabditis elegans* and *artemia salina* are abbreviated as C.E. and A.S., respectively.

TABLE 5

| Compound No. | C.E.(ng/ml) | A.S.(ng/ml) |
|---|---|---|
| B1a* | 2 | 0.5 |
| 2 | 2 | 0.5 |
| 7 | 0.1 | 0.02 |
| 9 | 2 | 2 |
| 10 | 0.5 | 0.5 |
| 12 | 2 | 0.5 |
| 36 | 2 | 0.5 |
| 39 | 0.5 | 0.1 |
| 40 | 2 | 0.5 |
| 43 | 2 | 0.5 |
| 45 | 0.5 | 0.5 |
| 47 | 2 | 2 |

*Positive Control (compound having OH at 4"-position)

INDUSTRIAL APPLICABILITY

According to the present invention, avermectin derivatives and salts thereof having antiparasitic activity are provided. The aforementioned derivatives and salts thereof are useful as active ingredients of antiparasitic agents.

What is claimed is:

1. A compound represented by the general formula (I) or a salt thereof:

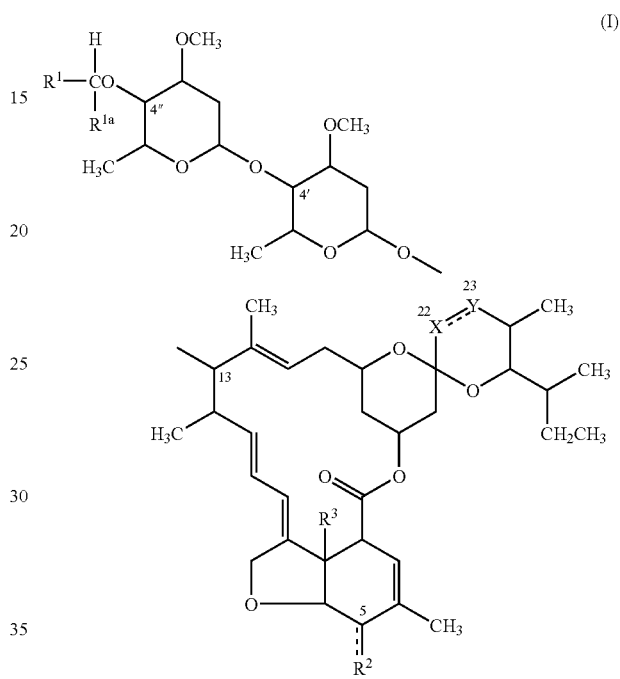

(I)

wherein, —X-----Y— represents —CH=CH—, —CH$_2$—C(=O)—, —CH$_2$—CH$_2$—, —CH$_2$—CH(R$^{13}$)— (wherein R$^{13}$ represents a hydroxyl group or a lower alkylcarbonyloxy group) or —CH$_2$—C(=N—CR$^{13c}$)— (wherein R$^{13c}$ represents a hydrogen atom or a lower alkyl group), -----between R$^2$ and the carbon atom at 5-position represents a single bond or a double bond, R$^1$ represents a substituted lower alkyl group, a formyl group, a carboxyl group, a lower alkoxycarbonyl group (wherein a lower alkyl moiety of said lower alkoxycarbonyl group may be substituted with a heterocyclic group), —CH=N—OR$^4$ (wherein R$^4$ represents a hydrogen atom or a lower alkyl group), a lower alkenyloxycarbonyl group, —CH=N—NH—CONH$_2$, a cyano group, —COR$^5$ (wherein R$^5$ represents an arylalkyloxy group (wherein the aryl group may contain one or more hetero atoms as ring-constituting atoms) or —NR$^6$R$^7$ (wherein R$^6$ and R$^7$ are combined together with the adjacent nitrogen atom to form a nitrogen-containing heterocyclic group), a vinyl group substituted with a lower alkenyloxycarbonyl group, —CO—S—CH$_2$—CH$_2$—NH—CO—R$^x$ (wherein R$^x$ represents a lower alkyl group), —CH=CH—COOH, or a substituted or unsubstituted aryl group, and R$^{1a}$ represents a hydrogen atom, provided that when R$^1$ represents a lower alkoxycarbonyl group (wherein a lower alkyl moiety of said lower alkoxycarbonyl group may be substituted with a heterocyclic group) or a carboxyl group, $R^{1a}$ may further represents a lower alkoxycarbonyl group (wherein a lower alkyl moiety of said lower alkoxycarbonyl group may be substituted with a heterocyclic group), a carboxyl group, a cyano group, or an aryl group, and provided that when —X⋯Y— is —CH$_2$—C(=O), —CH$_2$—CH$_2$, or =CH$_2$—CH($R^{13d}$)—(wherein $R^{13d}$ represents a lower alkylcarbonyloxy group), a substituent at the 4″-position may be a hydroxyl group instead of OCHR$^1$R$^{1a}$, when ⋯⋯between $R^2$ and the carbon atom at 5-position is a single bond, $R^2$ represents a hydroxyl group, a lower alkoxyl group, or a tri(lower alkyl)silyloxy group, and when ⋯⋯between $R^2$ and the carbon atom at the 5-position is a double bound, $R^2$ is combined with the carbon atom at 5-position to form a carbonyl group or a hydroxime group (—C(=NOH)), and $R^3$ represents a hydroxyl group or a tri(lower alkyl)silyloxy group.

2. The compound or a salt thereof according to claim 1, wherein $R^2$ is a hydroxyl group.

3. The compound or a salt thereof according to claim 1, wherein $R^2$ is combined with the carbon atom at 5-position to form a hydroxime group (—C(=NOH)).

4. The compound or a salt thereof according to claim 1, wherein $R^3$ is a hydroxyl group.

5. A medicament which comprises the compound according to claim 1 or a physiologically acceptable salt thereof as an active ingredient and a pharmaceutically acceptable additive.

6. A method for therapeutic treatment of parasitosis which comprises the step of administering to a mammal including a human a therapeutically effective amount of the compound or the physiologically acceptable salt thereof according to claim 1.

7. A method for the manufacture of the medicament of claim 5 comprising mixing the compound according to claim 1 or a pharmaceutically acceptable salt thereof with the pharmaceutically acceptable additive.

8. The method of claim 6 wherein the mammal is a human.

\* \* \* \* \*

UNITED STATES PATENT AND TRADEMARK OFFICE
CERTIFICATE OF CORRECTION

| | |
|---|---|
| PATENT NO. | : 7,144,866 B2 |
| APPLICATION NO. | : 10/343980 |
| DATED | : December 5, 2006 |
| INVENTOR(S) | : Satoshi Omura et al. |

It is certified that error appears in the above-identified patent and that said Letters Patent is hereby corrected as shown below:

On the Title Page:

Item (57), Abstract, formula (1) should appear as follows:

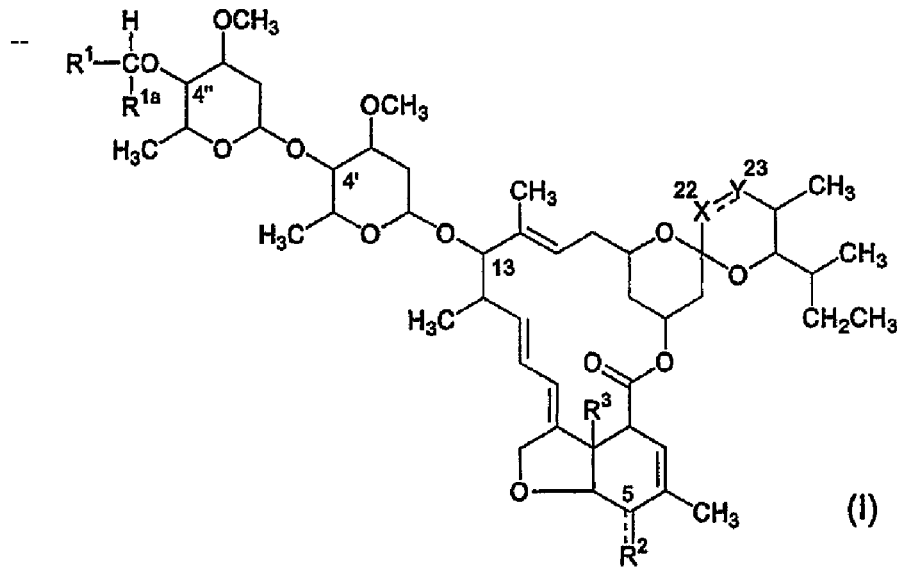

UNITED STATES PATENT AND TRADEMARK OFFICE
CERTIFICATE OF CORRECTION

PATENT NO.       : 7,144,866 B2
APPLICATION NO.  : 10/343980
DATED            : December 5, 2006
INVENTOR(S)      : Satoshi Omura et al.

It is certified that error appears in the above-identified patent and that said Letters Patent is hereby corrected as shown below:

In the Specification:

Column 1, lines 35-60, formula (I) should appear as follows:

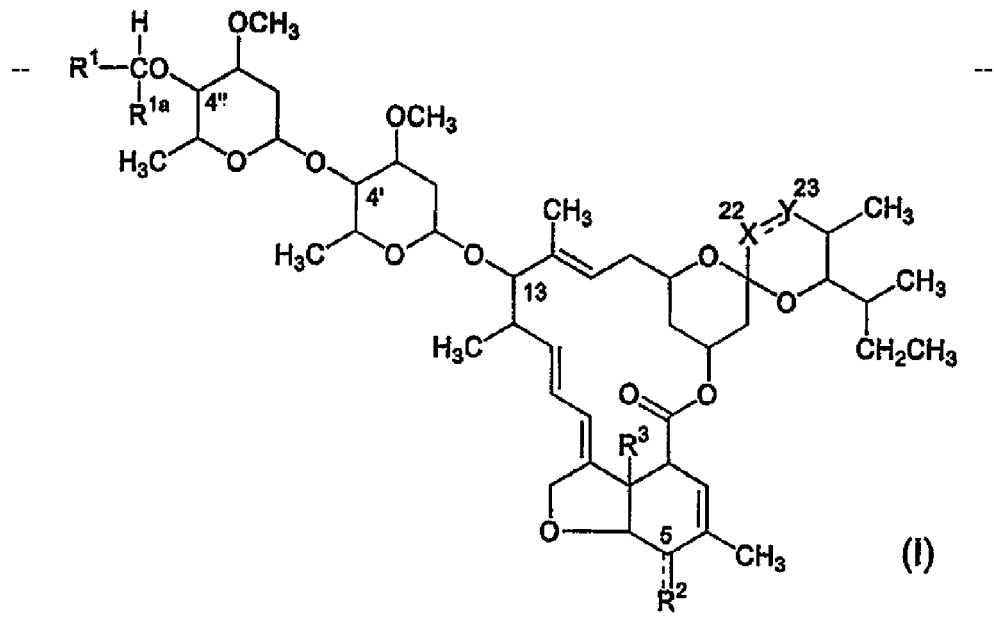

UNITED STATES PATENT AND TRADEMARK OFFICE
CERTIFICATE OF CORRECTION

PATENT NO. : 7,144,866 B2
APPLICATION NO. : 10/343980
DATED : December 5, 2006
INVENTOR(S) : Satoshi Omura et al.

It is certified that error appears in the above-identified patent and that said Letters Patent is hereby corrected as shown below:

In the Claims:

In Claim 1, at column 46, lines 10-38, formula (I) should appear as follows:

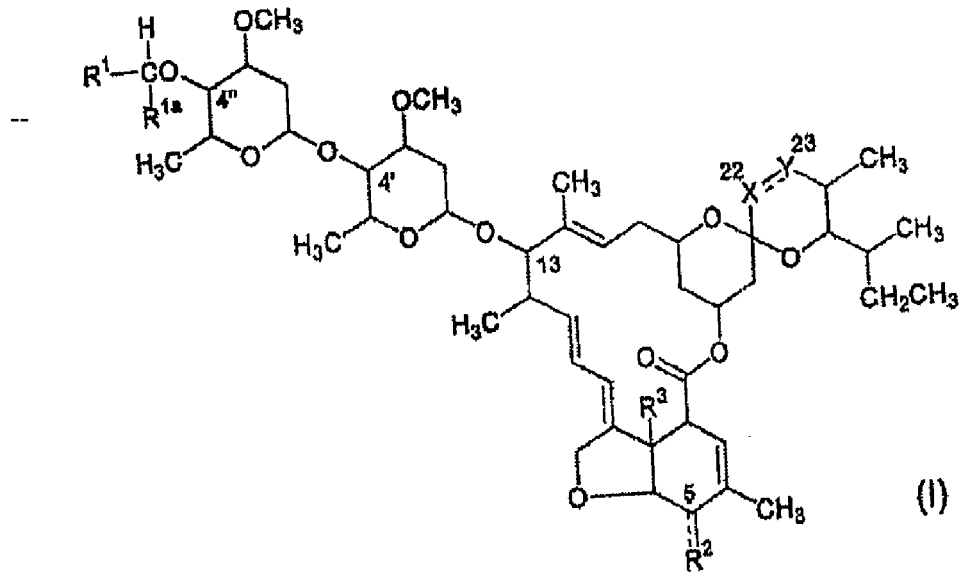

In Claim 1, at column 46, line 43, "$CR^{13c}$)- (wherein $R^{13c}$ represents a hydrogen atom or" should read -- $OR^{13c}$)- (wherein $R^{13c}$ represents a hydrogen atom or --.

Signed and Sealed this

Twenty-second Day of May, 2007

JON W. DUDAS
*Director of the United States Patent and Trademark Office*